(12) United States Patent
Shimomoto et al.

(10) Patent No.: US 7,938,025 B2
(45) Date of Patent: May 10, 2011

(54) ARRAY TYPE CAPACITANCE SENSOR

(75) Inventors: Yasushi Shimomoto, Kyoto (JP); Daisuke Kuzuyama, Kyoto (JP); Satoshi Nozoe, Kyoto (JP); Masao Hashimoto, Kyoto (JP); Kazunobu Itonaga, Kyoto (JP)

(73) Assignees: OMRON Corporation, Kyoto (JP); OMRON Healthcare Co., Ltd., Kyoto (JP)

( * ) Notice: Subject to any disclaimer, the term of this patent is extended or adjusted under 35 U.S.C. 154(b) by 0 days.

(21) Appl. No.: 12/301,596

(22) PCT Filed: May 15, 2007

(86) PCT No.: PCT/JP2007/059947
§ 371 (c)(1),
(2), (4) Date: Nov. 19, 2008

(87) PCT Pub. No.: WO2007/135895
PCT Pub. Date: Nov. 29, 2007

(65) Prior Publication Data
US 2009/0151478 A1  Jun. 18, 2009

(30) Foreign Application Priority Data
May 24, 2006  (JP) ................................. 2006-144680

(51) Int. Cl.
*G01L 1/14* (2006.01)
*G01L 1/00* (2006.01)
(52) U.S. Cl. .............................. 73/862.046; 73/862.626
(58) Field of Classification Search ............. 73/862.626, 73/862.046
See application file for complete search history.

(56) References Cited

U.S. PATENT DOCUMENTS

| | | | |
|---|---|---|---|
| 3,565,195 A * | 2/1971 | Miller et al. | 177/210 R |
| 4,644,801 A * | 2/1987 | Kustanovich | 73/862.046 |
| 5,533,515 A * | 7/1996 | Coller et al. | 600/593 |
| 5,799,533 A * | 9/1998 | Seki et al. | 73/172 |
| 6,626,046 B2 * | 9/2003 | Taguchi et al. | 73/753 |
| 7,069,791 B2 * | 7/2006 | Hashimoto et al. | 73/780 |
| 7,414,548 B2 * | 8/2008 | Volckers | 341/22 |
| 2004/0206190 A1 | 10/2004 | Kawahata | |
| 2004/0237669 A1 * | 12/2004 | Hayward et al. | 73/862.624 |
| 2005/0038347 A1 | 2/2005 | Suzuki et al. | |
| 2005/0257628 A1 * | 11/2005 | Nikaido et al. | 73/862.541 |
| 2006/0005631 A1 | 1/2006 | Hashimoto et al. | |
| 2009/0004767 A1 * | 1/2009 | Parks et al. | 438/53 |

FOREIGN PATENT DOCUMENTS

JP  62-204102  9/1987

(Continued)

OTHER PUBLICATIONS

International Search Report for International Application No. PCT/JP2007/059947, mailed on Jun. 19, 2007 (3 pages).

(Continued)

*Primary Examiner* — Lisa M Caputo
*Assistant Examiner* — Jonathan Dunlap
(74) *Attorney, Agent, or Firm* — Osha • Liang LLP

(57) ABSTRACT

In an array type capacitance sensor (1), a slit (2b) is provided between each pair of adjacent ones of multiple movable electrodes (6) on a movable-electrode-side substrate (2) so as to extend in parallel with the movable electrodes (6). This allows providing an array type capacitance sensor capable of being produced inexpensively and measuring pressure precisely and stably even on a curved surface.

6 Claims, 28 Drawing Sheets

FOREIGN PATENT DOCUMENTS

| | | |
|---|---|---|
| JP | 6-17838 | 3/1994 |
| JP | 08-274573 A | 10/1996 |

OTHER PUBLICATIONS

Patent Abstracts of Japan for Japanese Publication No. 62-298736, Publication date Dec. 25, 1987 (1 page) (Corresponds to JP6-17838).

R.S. Fearing, "Tactile Sensing Mechanisms", The International Journal of Robotics Research, Jun. 1990, vol. 9, No. 3, pp. 3-23 (21 pages).

D.A. Kontarinis et al., "A Tactile Shape Sensing and Display System for Teleoperated Manipulation", IEEE International Conference on Robotics and Automation, 1995, pp. 641-646 (6 pages).

Notice of Preliminary Rejection to Korean Patent Application No. 10-2008-7029009 mailed on Nov. 29, 2010 and English translation thereof, 8 pages.

* cited by examiner

F I G. 5
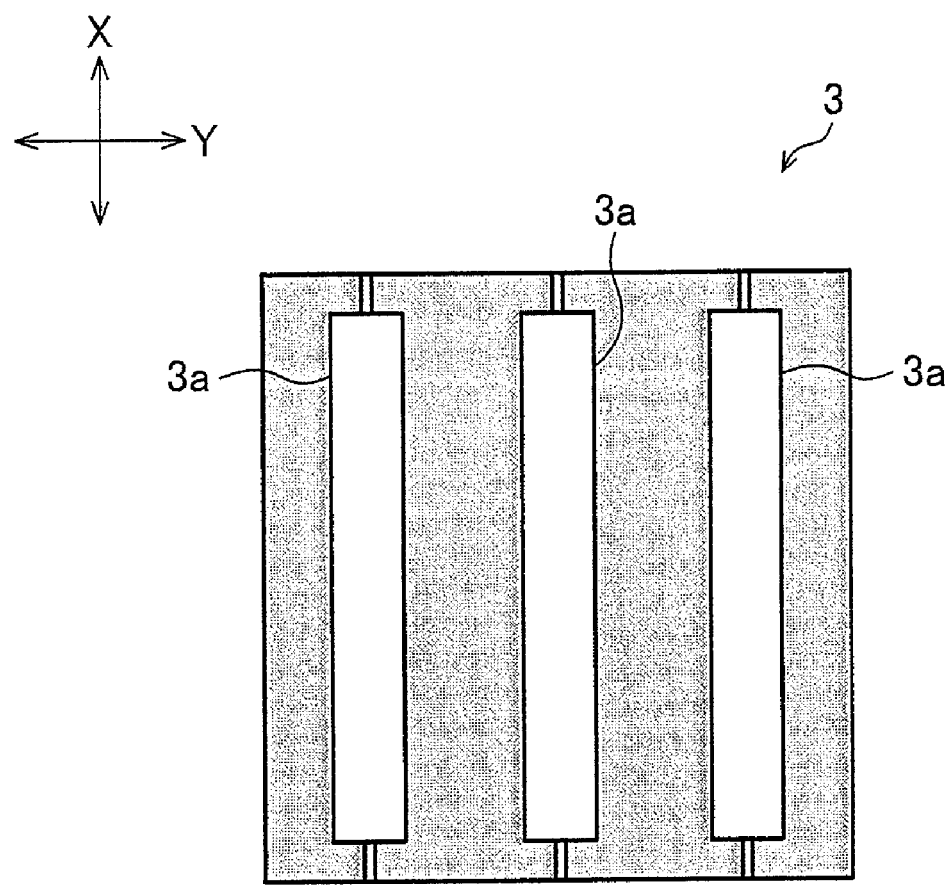

(a)

(b)

(a)

(b)

(a)

(b)

(a)

(b)

(c)

(d)

(a)

(b)

(c)

(d)

(Prior Art)

(Prior Art)

(Prior Art)

(Prior Art)

(Prior Art)

(a)

(b)

(Prior Art)

ARRAY TYPE CAPACITANCE SENSOR

TECHNICAL FIELD

The present invention relates to sensors for measurement of pressure fluctuating waveform, and in particular, to an array type capacitance sensor.

BACKGROUND ART

Generally, known sensing methods for measuring pressure include, besides a sensing system using a strain-resistant element, a sensing system using a capacitance element. According to the sensing system using a capacitance element, the structure of a sensor element is simpler than that of a sensor element in the sensing system using a strain-resistant element. Thus, the sensing system using a capacitance element has an advantage of being capable of inexpensively producing the sensor element, without the use of a semiconductor production process which requires a high production cost.

For example, touch sensors disclosed in Non-Patent Documents 1 and 2 are known as the sensing system using a capacitance element. Each of the touch sensors is a pressure sensor including capacitance elements arranged in an arrayed manner on its sensing surface, and is thus suitable for measurement of pressure fluctuating waveform.

The following description deals in detail with the touch sensor disclosed in Non-Patent Document 2. FIG. 26 is an outline perspective view of a pressure detection section in the touch sensor disclosed in Non-Patent Document 2. FIG. 27 is an exploded perspective view of the pressure detection section illustrated in FIG. 26. FIG. 28 (a) is a top plan view of the pressure detection section illustrated in FIG. 26. FIG. 28 (b) is a view illustrating a layout of capacitance elements in the pressure detection section. FIG. 29 is a circuit diagram of the touch sensor including the pressure detection section illustrated in FIG. 26.

As illustrated in FIGS. 26 and 27, a touch sensor 1E disclosed in Non-Patent Document 2 mainly includes: lower electrodes 11; upper electrodes 21; and spacer members 31. The lower electrodes 11 are made up of a plurality of strip-shaped copper foil electrodes which are provided in rows so as to substantially linearly extend in parallel with one another. The upper electrodes 21 are made up of a plurality of strip-shaped copper foil electrodes which are provided in columns so as to substantially linearly extend in parallel with one another. The upper electrodes 21 are disposed in a direction at right angles to the direction in which the lower electrodes 11 are disposed. The lower electrodes 11 and the upper electrodes 21 are separated from each other by the spacers 31 made of silicon rubber.

At intersections of the lower electrodes 11 and the upper electrodes 12, both of which are arranged in a matrix manner, portions of the lower electrodes 11 and portions of the upper electrodes 21 are disposed a predetermined distance apart from each other due to the spacers 31 such that the portions face each other, respectively. This allows capacitance elements 41 (see FIG. 28 (a)), each serving as a sensor element, to be formed at the intersections, respectively.

As illustrated in FIGS. 28 (a) and 28 (b), in the touch sensor 1E having the above arrangement, the capacitance elements 41 are arranged in an arrayed manner when the pressure detection section is observed from above. Respective capacitances of the capacitance elements 41 are changed in response to pressure which causes the upper electrodes 21 or the lower electrodes 11 to strain in a direction in which the upper electrodes 21 and the lower electrodes 11 become closer to each other.

In view of this, it is possible to obtain, by adopting a circuitry illustrated in FIG. 29, the capacitance of a specific one of the capacitance elements 41 arranged in an arrayed manner. Specifically, according to the circuitry, ones of the lower electrodes 11 and the upper electrodes 21, which are arranged in a matrix manner, are connected with a power supply 60 via a multiplexer 50, and the other ones of the lower electrodes 11 and the upper electrodes 21 are connected with a detector 70 also via a multiplexer 50. With the circuitry, when the multiplexers 50 select a specific one of the lower electrodes 11 and a specific one of the upper electrodes 21, the specific one of the capacitance elements 41 is identified and the capacitance of the specific capacitance element 41 thus identified is obtained through the detector 70. More specifically, for example, as in FIG. 29, in a case where (i) a specific lower electrode 11 in the second row from the top and (ii) a specific upper electrode 21 in the third column from the left are selected, the capacitance of a specific capacitance element indicated by the reference numeral 42 is outputted. Consequently, it is possible to measure pressure applied to any point on the sensing surface of the touch sensor 1E.

Known as other arts for measuring pressure fluctuating waveform are a surface pressure distribution sensor, disclosed in Patent Document 1, which uses a capacitance element, and a pressure pulse wave sensor and a pressure pulse wave analyzation apparatus described in Patent Document 2, both of which use a piezoelectric sheet.

FIG. 30 is a view illustrating a schematic arrangement of the surface pressure distribution sensor of Patent Document 1. As illustrated in FIG. 30, a surface pressure distribution sensor 101 includes a row wiring section 11 and a column wiring section 12. The row wiring section 11 and the column wiring section 12 are provided a predetermined distance apart from each other via a spacer 18 so as to face each other. The row wiring section 11 includes: a glass substrate 13; a lot of row wires 14 on the glass substrate 13; and an insulating film 15 covering the row wires 14. The row wires 14 are provided in parallel with one another in a first direction. The column wiring section 12 includes: a flexible film 16; and a lot of column wires 17 on the flexible film 16. The column wires 17 are provided in parallel with one another in a second direction.

FIG. 31 is a view illustrating a schematic arrangement of the pressure pulse wave sensor of Patent Document 2. As illustrated in FIG. 31, a pressure pulse wave sensor 102 is formed so that a first sensor section 12 and a second sensor section 14 are stacked. The first sensor section 12 includes a plurality of strip-shaped piezoelectric sheets 16 and a flexible sheet 18. The plurality of piezoelectric sheets 16 are arranged in a width direction of the piezoelectric sheets 16, and are integrally fixed to the flexible sheet 18. The piezoelectric sheets 16 are fastened to a body surface so as to detect pulse waves of the living body. The second sensor section 14 has the same structure as the first sensor section 12, and is rotated in a horizontal plane by 90 degrees with respect to the first sensor section 12.

[Non-Patent Document 1]
R. S. Fearing, "Tactile Sensing Mechanisms", The International Journal of Robotics Research, June 1990, Vol. 9, No. 3, pp. 3-23

[Non-Patent Document 2]
D. A. Kontarinis et al., "A Tactile Shape Sensing and Display System for Teleoperated Manipulation", IEEE International Conference on Robotics and Automation, 1995, pp. 641-646

[Patent Document 1]
Japanese Unexamined Patent Application Publication No. 317403/2004 (Tokukai 2004-317403; published on Nov. 11, 2004)
[Patent Document 2]
Japanese Unexamined Patent Application Publication No. 208711/2004 (Tokukai 2004-208711; published on Jul. 29, 2004)

SUMMARY OF THE INVENTION

Unfortunately, the above conventional arrangements pose problems stated below.

As illustrated in FIGS. 32 (a) and 32 (b), in a case where a touch sensor having either of the respective arrangements of Non-Patent Documents 1 and 2 is attached to a concavo-convex section (i.e., to a curved surface), the substrates on which electrode patterns are formed are bent such that one of the substrates which lies on the inner diameter side is under compressive stress, and that the other substrate on the outer diameter side is under tensile stress. This causes a reduction in the distance between the electrodes facing each other. (a) of FIG. 32 illustrates a side surface of the touch sensor in a normal state (i.e., flat state). (b) of FIG. 32 is a side surface of the touch sensor in a curved state. The reduction in the distance causes the sensor characteristic in the curved state illustrated in (b) of FIG. 32 to be largely different from the sensor characteristic in the flat state illustrated in (a) of FIG. 32. This causes a problem that the sensitivity of the sensor is decreased. In addition, another problem occurs that an initial output is increased because measurement is made while the distance between the opposite electrodes is being reduced and compressive stress is being applied.

These problems are also shared by the sensors of Patent Documents 1 and 2. Specifically, according to the surface pressure distribution sensor disclosed in Patent Document 1, the individual column wires are, although disposed on the flexible film, not independent of one another. Further, according to the pressure pulse wave sensor disclosed in Patent Document 2, the piezoelectric sheets are arranged so as to be fixed to the flexible sheet or an elastic substrate. Therefore, there causes a problem that, in a case where the touch sensors are attached to a curved surface for measurement, the sensor characteristic is most likely to be changed.

The present invention has been accomplished in view of the problems discussed above. It is an object of the present invention to provide an array type capacitance sensor capable of being produced inexpensively and measuring pressure precisely and stably even on a curved surface.

In order to attain the object, an array type capacitance sensor of the present invention includes: a first substrate including at least two rows of first electrodes provided so as to extend in parallel with one another; and a second substrate, provided so as to face and be at a predetermined distance from the first substrate, including at least two columns of second electrodes which extend in parallel with one another in a direction crossing a direction in which the first electrodes extend, the first substrate or the second substrate including a substrate slit section provided between adjacent ones of the first electrodes or of the second electrodes, respectively, the substrate slit section having a slit shape, and extending in parallel with the first electrodes or in parallel with the second electrodes, respectively.

According to the above arrangement, the first substrate or the second substrate includes a substrate slit section provided between adjacent ones of the first electrodes or of the second electrodes, respectively, and the substrate slit section has a slit shape, and extends in parallel with the first electrodes or in parallel with the second electrodes, respectively.

This causes the substrate slit section to be positioned adjacent to individual capacitance elements formed by the first electrodes and the second electrodes. In other words, the substrate slit section is present between any specific one of the capacitance elements and at least one of capacitance elements which are adjacent to the above specific capacitance element.

Conventional array type capacitance sensors are arranged such that neither the first substrate nor the second substrate is provided with the substrate slit section, and that the substrate slit section is consequently absent between adjacent ones of the capacitance elements. This causes the first electrodes and the second electrodes, both of which are disposed so as to face each other, to be under tensile stress and compressive stress, respectively, or vice versa, in a case where the first substrate or the second substrate is deformed at a time of measuring pressure. This consequently causes the capacitance elements to be applied with pressure other than pressure from a measurement target, and thereby causes an initial output to be increased. As a result, it is impossible to measure pressure precisely and stably.

By contrast with this, in the array type capacitance sensor of the present invention, the substrate slit section is present between adjacent ones of the capacitance elements. This allows (i) the individual first electrodes to be deformed independently of adjacent ones of the first electrodes in a case where the first substrate is attached to a surface such as a bent surface for measurement of pressure and is thereby deformed, or (ii) the individual second electrodes to be deformed independently of adjacent ones of the second electrodes in a case where the second substrate is attached to a surface such as a bent surface for measurement of pressure and is thereby deformed. This consequently allows (i) a specific one of the capacitance elements which one coincides with a deformed portion of the first substrate to be influenced less by an adjacent portion of the first substrate and the first electrodes, or (ii) a specific one of the capacitance elements which one coincides with a deformed portion of the second substrate to be influenced less by an adjacent portion of the second substrate and the second electrodes. As a result, it is possible to precisely and stably measure pressure applied from a measurement target. In addition, cross talk can be reduced compared to conventional array type capacitance sensors due to the absence of the influence from an adjacent portion of the first or second substrate and the first or second electrodes. Furthermore, the simple arrangement of providing the first substrate or the second substrate with the substrate slit section allows inexpensively producing an array type capacitance sensor capable of measuring pressure precisely and stably.

The array type capacitance sensor of the present invention may preferably be arranged such that the substrate slit section is provided in a direction at right angles to a direction in which the first substrate or the second substrate is bent during measurement.

According to the above arrangement, the substrate slit section is provided in a direction at right angles to a direction in which the first substrate or the second substrate is bent during measurement.

In a case where, for example, the array type capacitance sensor is used to measure arterial pulse waves, the first substrate or the second substrate is bent so as to have a shape similar to outline of a wrist of a person to be tested. Note that the direction in which the first substrate or the second substrate is bent refers, in the case of the above example, to a direction in which the array type capacitance sensor is bent when attached to the wrist of the person to be tested. In other words, the bend direction refers to a direction which orthogonally crosses the direction an artery of the person to be tested extends.

In comparison to disposing the substrate slit section in the bend direction, disposing the substrate slit section in the direction which orthogonally crosses the bend direction allows reducing the influence of deformation of the first substrate or the second substrate, which influence is transmitted from adjacent ones of the capacitance elements to each other. This is because the first substrate or the second substrate is bent from the substrate slit section. This allows more precisely and more stably measuring pressure applied from a measurement target. In addition, cross talk can be reduced further since it is possible to reduce the influence, on a specific one of the capacitance elements, from an adjacent portion of the first or second substrate and the first or second electrodes.

The array type capacitance sensor of the present invention may preferably further include a spacer provided between the first substrate and the second substrate so as to maintain the predetermined distance, the spacer including spacer opening sections provided so as to extend, in a direction at right angles to a longitudinal direction of the substrate slit section, in projection areas of the first or second electrodes onto the spacer, respectively.

According to the above arrangement, the spacer includes spacer opening sections provided so as to extend, in a direction at right angles to a longitudinal direction of the substrate slit section, in projection areas of the first or second electrodes onto the spacer, respectively This causes the capacitance elements formed by the first electrodes and the second electrodes to be each surrounded by a combination of the substrate slit section and the spacer. In other words, adjacent ones of the capacitance elements are separated by either an opening section of the first or second substrate or the spacer. Therefore, adjacent ones of the capacitance elements which ones are not separated by the substrate slit section are separated by the spacer. This allows further reducing the influence of deformation of the first substrate or the second substrate, which influence is transmitted from adjacent ones of the capacitance elements to each other. As a result, it is possible to more precisely and more stably measure pressure applied from a measurement target. In addition, cross talk can be reduced further.

The array type capacitance sensor of the present invention may preferably be arranged such that the spacer includes a plurality of spacer slit sections, each having a slit shape, which are provided so as to extend, in parallel with the substrate slit section, in projection areas of the substrate slit section onto the spacer.

According to the above arrangement, the spacer is provided with the spacer slit sections extending in the same direction as the substrate slit section. This allows the first substrate or the second substrate to be readily deformed when pressure is measured. This consequently allows the first electrodes or the second electrodes to be readily deformed, and thereby allows improving the responsiveness of the array type capacitance sensor. In addition, cross talk can be reduced even further.

The array type capacitance sensor of the present invention may preferably further include a stabilizing member, the stabilizing member including grooves whose projection areas coincide with projection areas onto the substrate slit section, respectively, and the stabilizing member being provided, on a surface of the first substrate which surface is opposite to a surface facing the second substrate, or, on a surface of the second substrate which surface is opposite to a surface facing the first substrate According to the above arrangement, the array type capacitance sensor is provided with the stabilizing member which has the grooves extending in the same direction as the substrate slit section. This allows the first substrate or the second substrate to be readily deformed when pressure is measured. This consequently allows the first electrodes or the second electrodes to be readily deformed, and thereby allows improving the responsiveness of the array type capacitance sensor. As a result, it is possible to measure pressure more precisely and more stably. In addition, cross talk can be reduced further. Furthermore, the above arrangement allows maintaining the planarity of the first electrodes or the second electrodes both of which form the capacitance elements. This allows the first electrodes and the second electrodes to be held in parallel with each other, and thereby allows reducing change in the sensor characteristic which change occurs when the array type capacitance sensor is bent.

The array type capacitance sensor of the present invention may preferably be arranged such that the first or second substrate, which includes the substrate slit section, has flexibility.

According to the above arrangement, the first or second substrate, which includes the substrate slit section, has flexibility. This further allows the first or second substrate to be readily deformed when pressure is measured. This consequently allows the first or second electrodes to be more readily deformed, and thereby allows further improving the responsiveness of the array type capacitance sensor. As a result, it is possible to measure pressure more precisely and more stably. In addition, cross talk can be reduced further.

The array type capacitance sensor of the present invention may preferably be arranged such that the spacer has flexibility.

According to the above arrangement, the spacer has flexibility. This further allows the first substrate or the second substrate to be readily deformed when pressure is measured. This consequently allows the first electrodes or the second electrodes to be more readily deformed, and thereby allows further improving the responsiveness of the array type capacitance sensor. As a result, it is possible to measure pressure more precisely and more stably. In addition, cross talk can be reduced further.

Additional objects, features, and strengths of the present invention will be made clear by the description below. Further, the advantages of the present invention will be evident from the following explanation in reference to the drawings.

BRIEF DESCRIPTION OF THE DRAWINGS

FIG. 5 is a top plan view of a spacer included in the array type capacitance sensor of Embodiment 1.

FIG. 7 (b) is a sectional view illustrating the capacitance elements of the conventional array type capacitance sensor which capacitance elements are observed in a case where the conventional array type capacitance sensor is positioned on a surface to be detected.

FIG. 8 (b) is a sectional view illustrating the capacitance elements of the array type capacitance sensor 1 of Embodiment 1 which capacitance elements are observed in a case where the array type capacitance sensor is positioned on the surface to be detected.

FIG. 9 (b) is a graph showing the relationship between pressure and capacitance in the array type capacitance sensor of Embodiment 1, in which slits are provided on the movable-electrode-side substrate.

FIG. 28 (b) is a view illustrating a layout of capacitance elements in the capacitance pressure sensor illustrated in FIG. 26.

Figure 1:
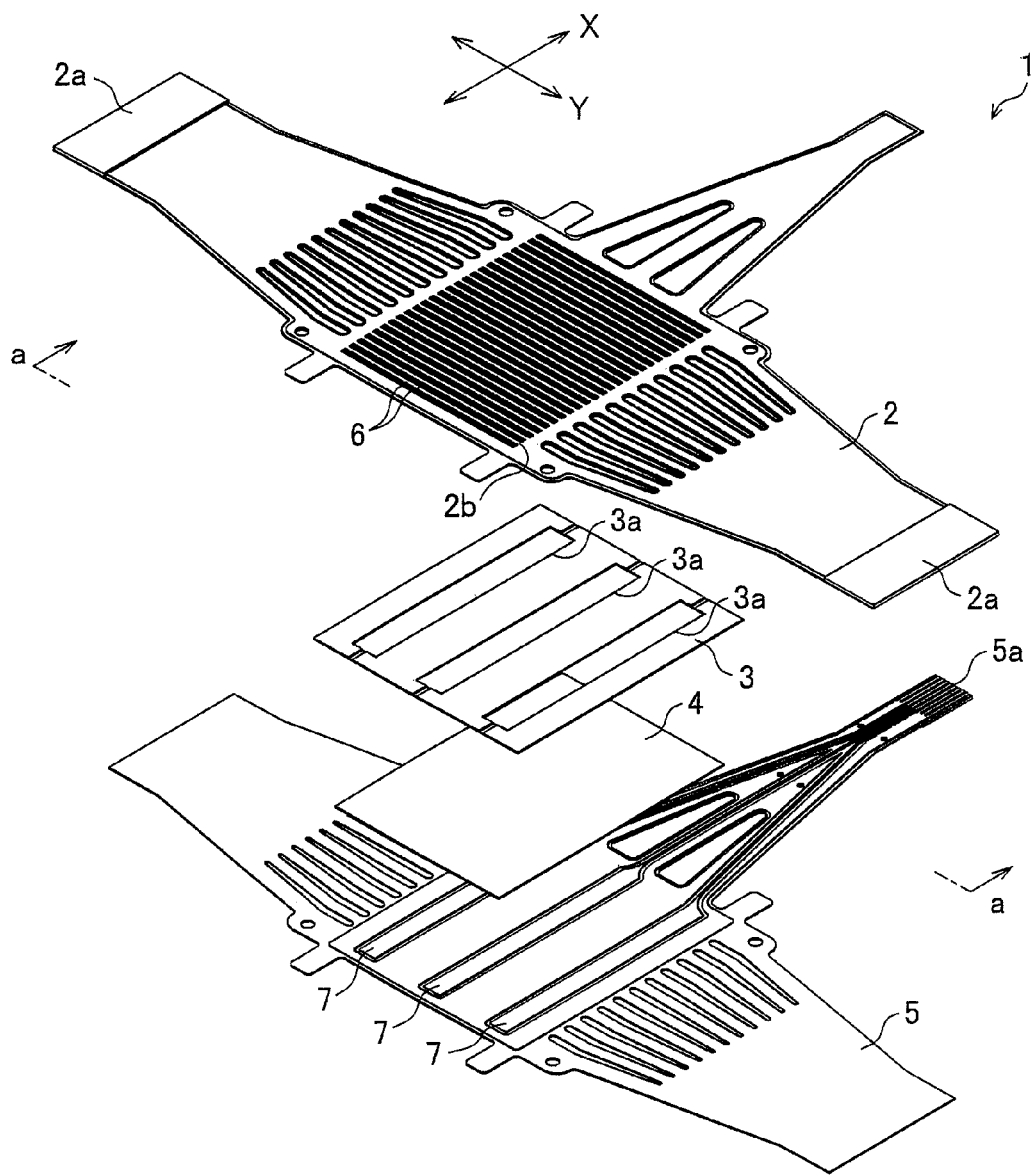
FIG. 1 is an exploded perspective view of an array type capacitance sensor in accordance with Embodiment 1 of the present invention.

DESCRIPTION OF THE REFERENCE NUMERALS 1, 20, 30, 40 Array type capacitance sensor
2 Movable-electrode-side substrate (first substrate, second substrate)
2b Slit (substrate slit section)
3 Spacer
3a Opening section (spacer opening section)
3b Slit (spacer slit section)
5 Fixed-electrode-side substrate (first substrate, second substrate)

6 Movable electrode (first electrode, second electrode)
7 Fixed electrode (first electrode, second electrode)
8 Stabilizing member
8c Groove

DETAILED DESCRIPTION

One embodiment of the present invention is described below with reference to the attached drawings. Array type capacitance sensors are applicable in various fields as sensors detecting physical quantity through changes in capacitance. The present embodiment deals with, as an example of such applications, a case of measuring waveform of intra-arterial pressure in a living body.

First, an outline of an array type capacitance sensor of the present embodiment will be briefly explained.

The array type capacitance sensor of the present embodiment is capable of measuring waveform of intra-arterial pressure when, for example, pressed against a body surface of a living body. The array type capacitance sensor includes: a fixed-electrode-side substrate; a movable-electrode-side substrate; and 72 capacitance elements. The fixed-electrode-side substrate is provided with three rows of fixed electrodes provided in parallel with one another so as to, when the array type capacitance sensor is pressed against a body surface of a living body, linearly extend in a direction substantially orthogonal to a direction in which an artery of the living body extends. The movable-electrode-side substrate is provided with 24 columns of movable electrodes provided a predetermined distance apart from the fixed electrodes so as to face the fixed electrodes, respectively. The movable electrodes are provided in parallel with one another so as to extend in a direction at right angles to the direction in which the fixed electrodes extend. The capacitance elements are formed at intersections of the three rows of fixed electrodes and the 24 columns of movable electrodes, respectively. In addition, slits are secured between adjacent ones of the 24 columns of movable electrodes, respectively. The individual movable electrodes can be deformed independently of one another in response to the pressure applied to the movable-electrode-side substrate.

In general, an array type capacitance sensor, for use in measurement of waveform of intra-arterial, receives pressure from above which is generated by, for example, an air bag so as to be pressed against a body surface of a living body. This causes each capacitance of the capacitance elements to be detected while the movable-electrode-side substrate is being in close contact with a portion (concavoconvex shape) to be measured on the body surface. This allows intra-arterial pressure to be measured.

The following description deals with a detailed arrangement of the array type capacitance sensor of the present embodiment. Note that the terms defined in Embodiment 1 are also used in other embodiments (later described), in accordance with the definitions in Embodiment 1, unless otherwise noted.

EMBODIMENT 1

Figure 2:
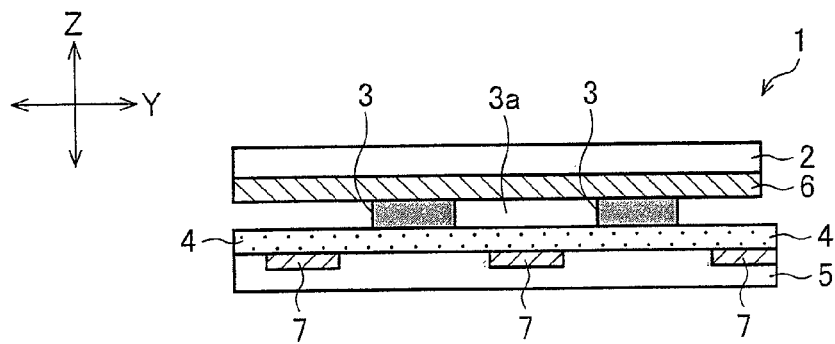
FIG. 2 is a partial sectional view of the array type capacitance sensor according to Embodiment 1, taken along the line a-a of FIG. 1.

FIG. 1 is an exploded perspective view of an array type capacitance sensor according to Embodiment 1 of the present invention. FIG. 2 is a partial sectional view of the array type capacitance sensor, taken along the line a-a of FIG. 1. As illustrated in FIGS. 1 and 2, an array type capacitance sensor 1 includes: a movable-electrode-side substrate 2; a spacer 3; a dielectric film 4; and a fixed-electrode-side substrate 5.

The movable-electrode-side substrate (first substrate, second substrate) 2 is brought into contact with a target surface to be detected (in the present embodiment, a body surface of a living body) so as to receive intra-arterial pressure. The movable-electrode-side substrate 2 includes movable electrodes (first electrodes, second electrodes) 6, and connector connection sections 2a. The movable electrodes 6 are flexible and have a sheet shape. The movable electrodes 6 are provided on a side of the movable-electrode-side substrate 2 which side is opposite from a side facing the target surface to be detected. The connector connection sections 2a are provided at both ends of the movable electrodes 6. The movable-electrode-side substrate 2 can be an insulative glass-epoxy substrate, or can be made up of material such as a polyimide film, a PET film, or an epoxy resin film. The movable-electrode-side substrate 2 and the movable electrodes 6 will be later described in detail.

The fixed-electrode-side substrate (first substrate, second substrate) 5 is provided so as to face the side of the movable-electrode-side substrate 2 which side is opposite from the side facing the target surface to be detected so as to face the movable-electrode-side substrate 2. The fixed-electrode-side substrate 5 includes fixed electrodes (first electrodes, second electrodes) 7, and a connector connection section 5a at an end of the fixed electrodes 7. As in the movable-electrode-side substrate 2, the fixed-electrode-side substrate 5 can be an insulative glass-epoxy substrate, or can be made up of material such as a polyimide film, a PET film, or an epoxy resin film. The fixed-electrode-side substrate 5 and the fixed electrodes 7 will be later described in detail.

The spacer 3 is made of material such as silicon rubber. The spacer 3 is provided so as to maintain a predetermined distance (gap) between the movable-electrode-side substrate 2 and the fixed-electrode-side substrate 5. By maintaining the gap (space) between the movable-electrode-side substrate 2 and the fixed-electrode-side substrate 5, the spacer 3 maintains a gap between the movable electrodes 6 and the fixed electrodes 7. The size of the gap is optionally set depending on (i) a range of physical quantities to be detected by the array type capacitance sensor 1 and (ii) the amount of deformation of the movable-electrode-side substrate 2. The spacer 3 will be later described in detail.

The dielectric film 4 is for preventing a short circuit caused by contact between a movable electrode 6 of the movable-electrode-side substrate 2 and a fixed electrode 7 of the fixed-electrode-side substrate 5. The dielectric film 4 is also for increasing capacitance. The dielectric film 4 is preferably small in thickness, and is made of, for example, an epoxy film having a thickness of 20 μm.

Figure 3:
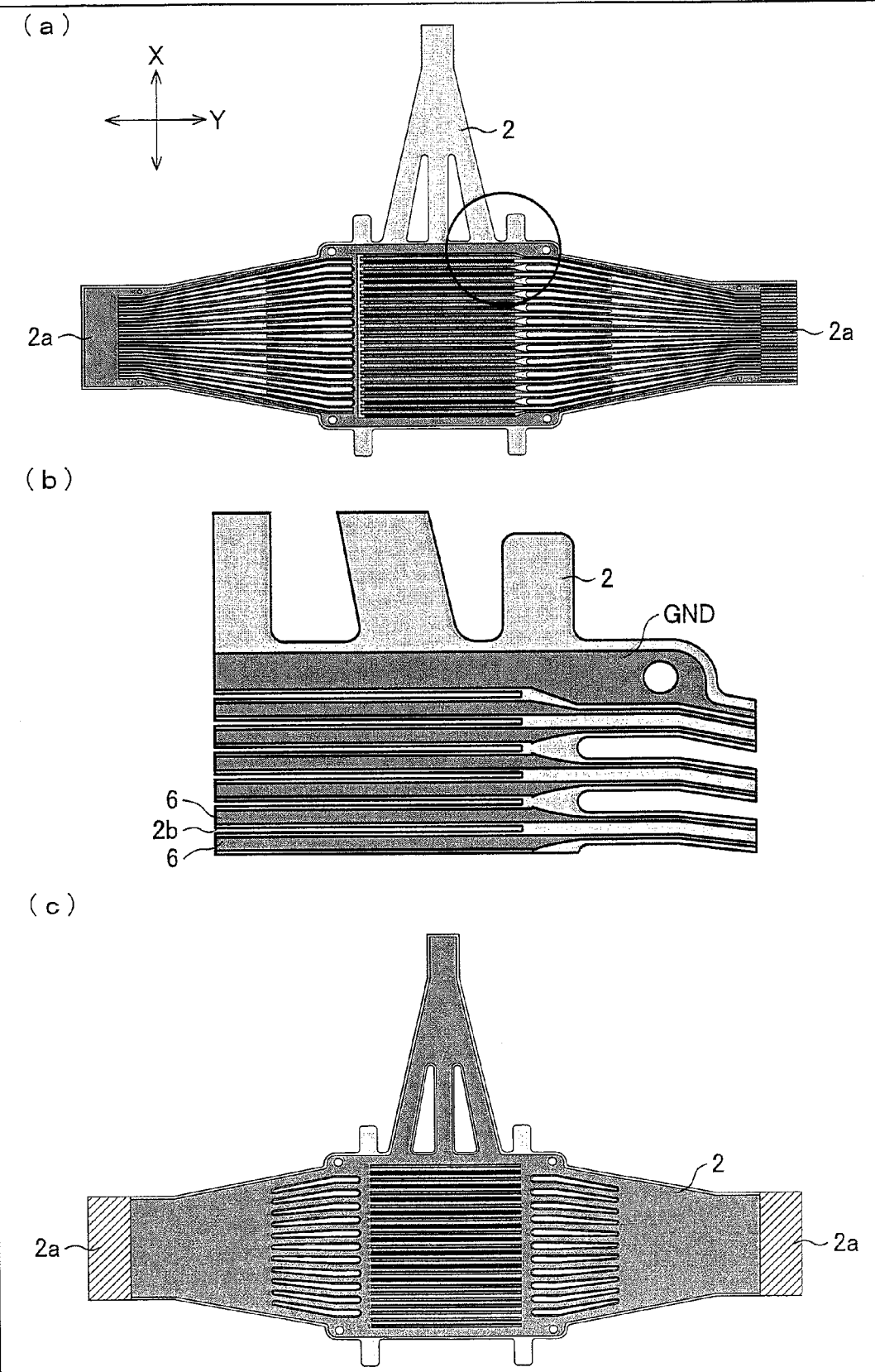
FIG. 3 is a view illustrating a movable-electrode-side substrate included in the array type capacitance sensor of Embodiment 1, (*a*) is a plan view obtained when the movable-electrode-side substrate is viewed from the side on which movable electrodes are provided, (*b*) is a partially enlarged view of (*a*), and (*c*) is a plan view obtained when the movable-electrode-side substrate is viewed from the side of the target surface to be detected (rear side).

With reference to FIG. 3, the following description deals with a detailed arrangement of each of the movable-electrode-side substrate 2, the fixed-electrode-side substrate 5, and the spacer 3.

FIG. 3 is a view illustrating the movable-electrode-side substrate in the array type capacitance sensor of Embodiment 1, (a) is a plan view obtained when the movable-electrode-side substrate 2 is viewed from the movable-electrode-side, (b) is a partially enlarged view of (a), and (c) is a plan view obtained when the movable-electrode-side substrate 2 is viewed from the side of the target surface to be detected (rear side). It is assumed in the present embodiment and other embodiments (later described), that the direction in which the plurality of strip-shaped electrodes extend, from which the movable electrodes 6 are formed, is indicated by the Y direction, and the direction orthogonal to the Y direction and in parallel with the surface of the movable-electrode-side substrate 2 is indicated by the X direction.

As illustrated in (a) and (b) of FIG. 3, the movable electrodes 6, made up of 24 rows of strip-shaped electrodes which linearly extend in the Y direction, are provided so as to be juxtaposed at even intervals and in parallel with one another. The present embodiment deals with the case where the movable electrodes 6 are made up of 24 rows of strip-shaped electrodes. However, the number of rows of strip-shaped electrodes is not limited to this, provided that the number is at least two. The movable electrodes 6 are made of material such as copper foil which is formed on the movable-electrode-side substrate 2 by sputtering or vapor deposition. The movable electrodes 6 are arranged so as to be capable of being deformed, following a deformation of the movable-electrode-side substrate 2 which occurs in response to pressure from a target surface to be detected. Each of the strip-shaped electrodes is connected, at its end, with either one of the two 12-channel connector connection sections 2a.

As illustrated in (b) and (c) of FIG. 3, the movable-electrode-side substrate 2 includes a plurality of slits (substrate slit sections) 2b provided for gaps between adjacent ones of the 24 rows of linearly extending strip-shaped electrodes, respectively. The slits 2b are disposed so as to linearly extend in parallel with one another. This allows each of the strip-shaped electrodes constituting the movable electrodes 6 to be deformed independently of adjacent ones of the strip-shaped electrodes, when pressure is applied to the movable-electrode-side substrate 2 from a target surface to be detected.

Figure 4:
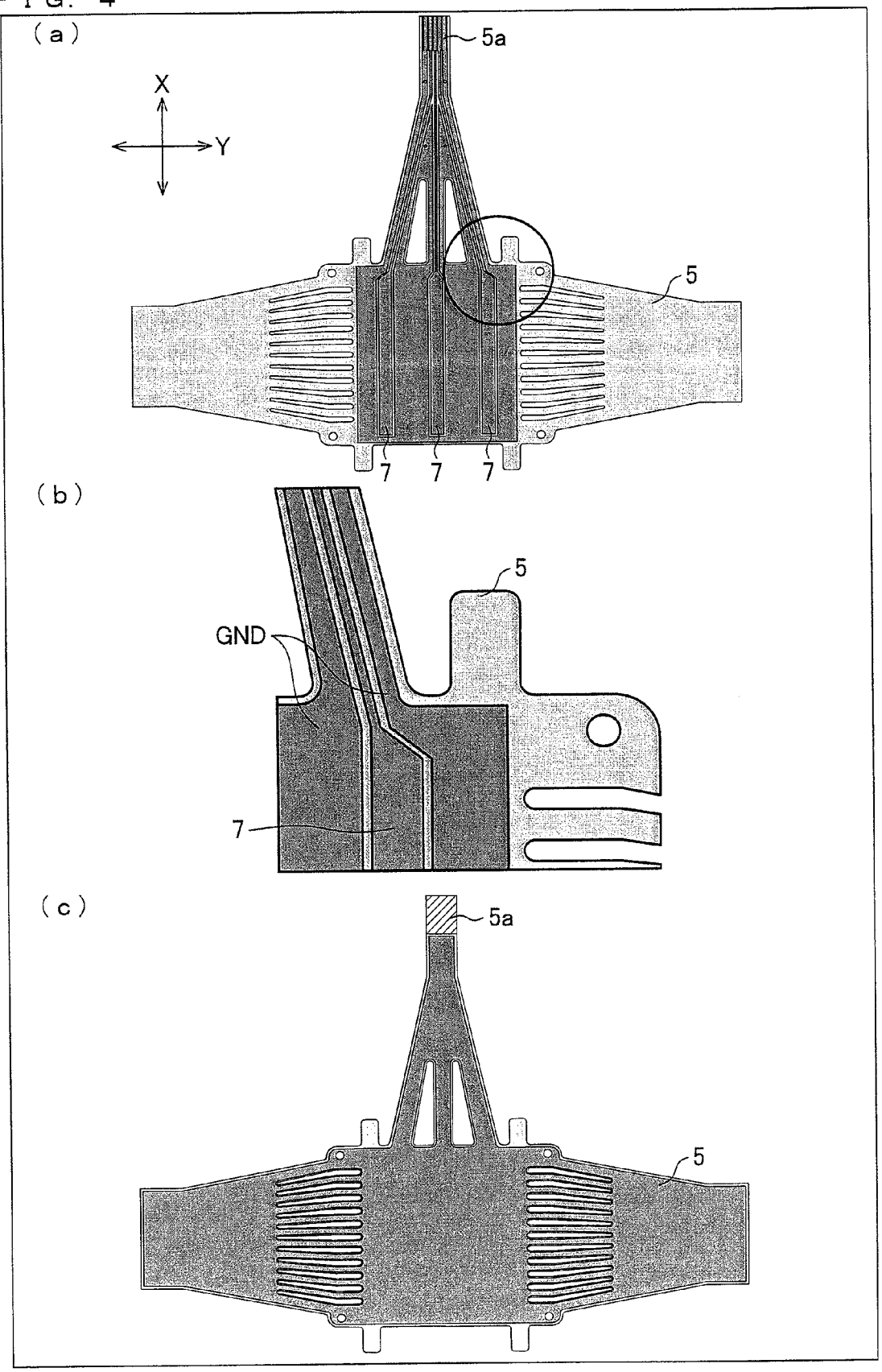
FIG. 4 is a view illustrating the movable-electrode-side substrate in the array type capacitance sensor of Embodiment 1, (*a*) is a plan view obtained when the fixed-electrode-side substrate is viewed from the fixed-electrode-side, (*b*) is a partially enlarged view of (a), and (c) is a plan view obtained when the fixed-electrode-side substrate is viewed from the side on which the fixed electrodes are not provided (rear side).

FIG. 4 is a view illustrating the movable-electrode-side substrate in the array type capacitance sensor of Embodiment 1, (a) is a plan view obtained when the fixed-electrode-side substrate 2 is viewed from the fixed-electrode-side, (b) is a partially enlarged view of (a), and (c) is a plan view obtained when the fixed-electrode-side substrate 2 is viewed from the side on which the fixed electrodes are not provided (rear side).

As illustrated in (a) and (b) of FIG. 4, the fixed electrodes 7, made up of three columns of strip-shaped electrodes which linearly extend in the X direction, are provided so as to be juxtaposed at even intervals and in parallel with one another. The present embodiment deals with the case where the fixed electrodes 7 are made up of three columns of strip-shaped electrodes. However, the number of columns of strip-shaped electrodes is not limited to this, provided that the number is at least two. The fixed electrodes 7 are made of material such as copper foil which is formed on the fixed-electrode-side substrate 5 by sputtering or vapor deposition. The fixed electrodes 7 are arranged so that no pressure is applied to the fixed electrodes 7 from a target surface to be detected. Each of the strip-shaped electrodes is connected, at its end, with the 3-channel connector connection section 5a.

FIG. 5 is a top plan view of the spacer 3. The spacer 3 is provided between the movable-electrode-side substrate 2 and the fixed-electrode-side substrate 5 so as to maintain a constant distance between the movable-electrode-side substrate 2 and the fixed-electrode-side substrate 5. The spacer 3 is provided with three columns of opening sections (spacer opening sections) 3a. The opening sections 3a linearly extend in the X direction, and positionally correspond to the fixed electrodes 7 so that the spacer 3 does not cover the fixed electrodes 7. The opening sections 3a each preferably have a width and a length which are equal to or are greater than the width and the length of the individual fixed electrodes 7.

The following description deals with how the array type capacitance sensor 1, including the above constituent members, is assembled.

As illustrated in FIG. 1, the movable-electrode-side substrate 2 including the movable electrodes 6 and the fixed-electrode-side substrate 5 including the fixed electrodes 7 are stacked such that the strip-shaped electrodes, i.e., the 24 rows of strip-shaped electrodes and the three columns of strip-shaped electrodes, intersect with each other when being viewed from above. The spacer 3 is provided between the movable-electrode-side substrate 2 and the fixed-electrode-side substrate 5 such that the opening sections 3a of the spacer 3 and the fixed electrodes 7 of the fixed-electrode-side substrate 5 coincide with each other. A dielectric sheet is further provided between the movable-electrode-side substrate 2 and the fixed-electrode-side substrate 5. These constituent members are deposited one after another by a method such as sputtering or vapor deposition, and then all of the constituent members are stacked and combined with each other.

In the array type capacitance sensor 1 thus assembled, at the intersections of the movable electrodes 6 and fixed electrodes 7 which are provided in a matrix manner, a predetermined distance (e.g., about 100 μm) is maintained, by the spacer 3 made of material such as silicon rubber, between the intersections of the movable electrodes 6 and fixed electrodes 7. The above predetermined distance allows spaces to be formed at the intersections, respectively. This causes a portion of the movable electrodes 6 and a portion of the fixed electrodes 7 to be provided so as to face each other across the space. Consequently, a capacitance element serving as a sensor element is formed at each of the intersections. The array type capacitance sensor 1 of the present embodiment, which includes three rows and 24 columns of electrodes, has 72 capacitance elements formed in total.

Figure 6:
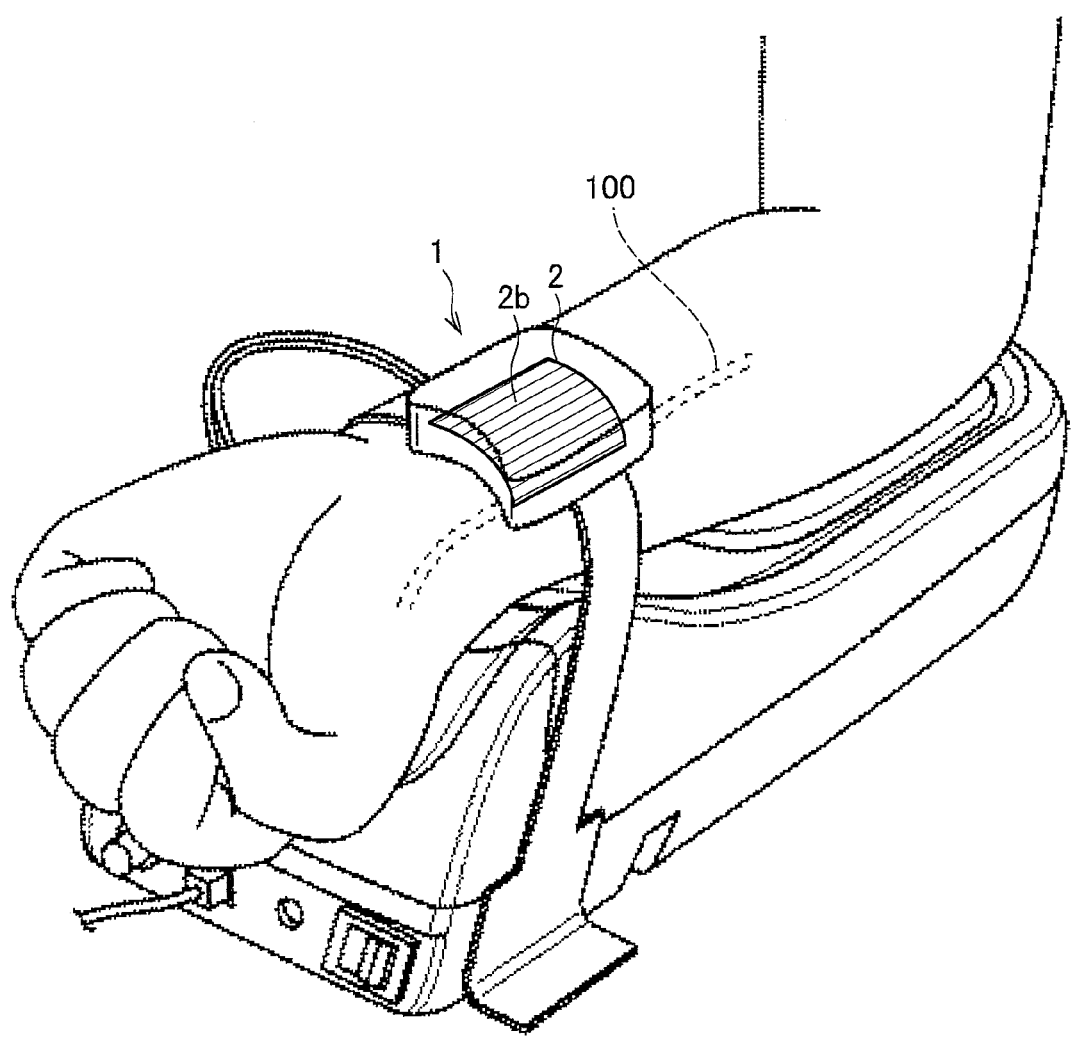
FIG. 6 is a view illustrating the movable-electrode-side substrate observed in a case where a person to be tested wears, on a body surface (wrist), the array type capacitance sensor of Embodiment 1.

The following description deals with a use method and principle of the array type capacitance sensor 1. FIG. 6 is a view illustrating the movable-electrode-side substrate 2 observed in a case where a person to be tested wears, on a body surface (e.g., wrist), the array type capacitance sensor 1.

As illustrated in FIG. 6, the person to be tested wears, on the wrist, the array type capacitance sensor 1 while pressing against the wrist the surface of the movable-electrode-side substrate 2, which surface is on the opposite side of the surface on which the movable electrodes 6 are provided. The array type capacitance sensor 1 is worn such that the longitudinal direction of the linear slits 2b in the movable-electrode-side substrate 2 substantially matches a direction in which an artery 100 of the person to be tested extends. Pressing force is applied, from above, to the fixed-electrode-side substrate 5 from an air bag 1a (see FIG. 7 (b)) so that the movable-electrode-side substrate 2 is in close contact with the wrist. Since the array type capacitance sensor 1 is worn such that movable-electrode-side substrate 2 is pressed against the target surface (wrist) 1b to be detected (see FIG. 7 (b)), the movable-electrode-side substrate 2 and the movable electrodes 6 are deformed so as to have a shape similar to outline of the wrist. The movable-electrode-side substrate 2 is provided with the slits 2b which extend in parallel with the strip-shaped electrodes constituting the movable electrodes 6. As such, unlike conventional array type capacitance sensors, the deformation, occurring when the array type capacitance sensor 1 is worn, does not cause the strip-shaped electrodes to be under compressive stress or tensile stress.

In consequence, the movable electrodes 6 forming the capacitance elements are deformed toward the fixed electrodes 7 when the movable electrodes 6 receive intra-arterial pressure from the wrist. The deformations of the movable electrodes 6 cause changes in the distances between the movable electrodes 6 and the fixed electrodes 7, and thereby causing changes in the capacitances (charged electricity), respectively. It is possible to detect pressure applied to the movable-electrode-side substrate 2 in accordance with conversions of such changes in the capacitances into voltages.

As described above, according to the array type capacitance sensor 1 of the present embodiment, in a case where the movable-electrode-side substrate 2 is attached to the surface 1b to be detected such that the longitudinal direction of the linear slits 2b in the movable-electrode-side substrate 2 substantially matches the direction in which the artery 100 of the person to be tested extends, the strip-shaped electrodes constituting the movable electrodes 6 are deformed independently of one another so as to have a shape similar to outline of the surface 1b to be detected. As such, the capacitance elements formed in the array type capacitance sensor 1 do not affect one another while the deformations of the strip-shaped electrodes are occurring. This will be explained below in further detail with reference to FIGS. 7 and 8.

Figure 7:
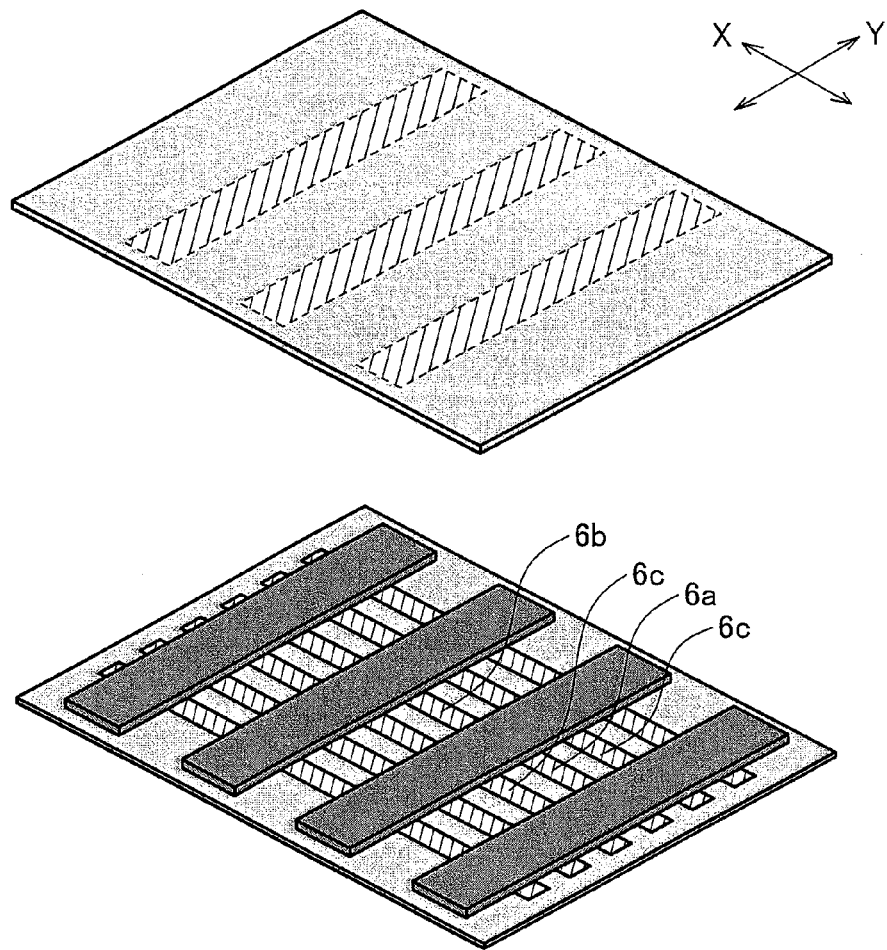
FIG. 7 (a) is an exploded perspective view illustrating capacitance elements in a conventional array type capacitance sensor.
Figure 7:
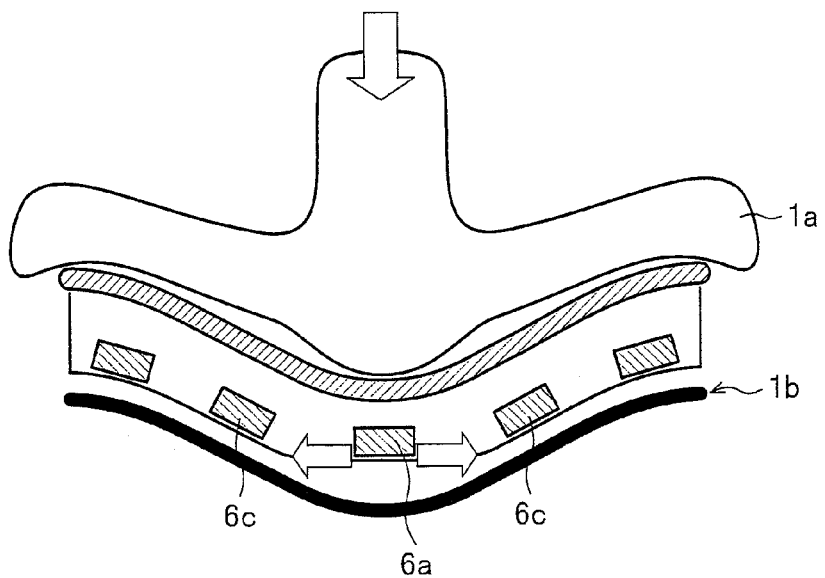
Figure 8:
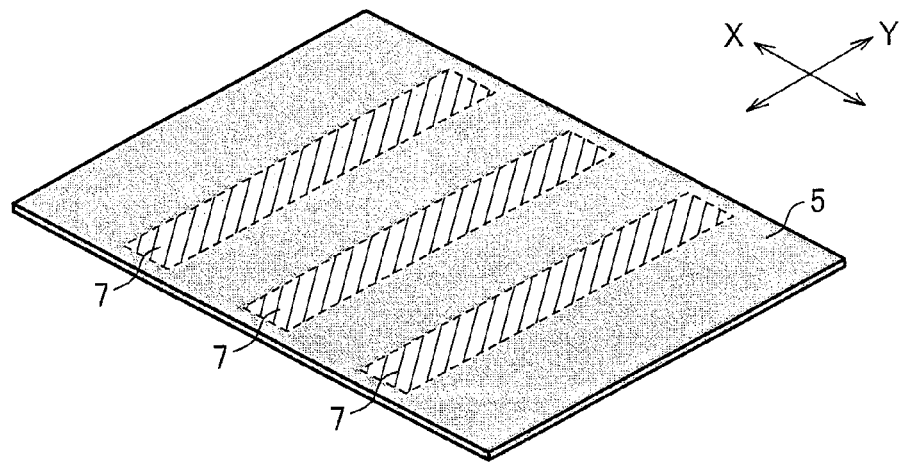
FIG. 8 (a) is an exploded perspective view illustrating capacitance elements in the array type capacitance sensor of Embodiment 1.
Figure 8:
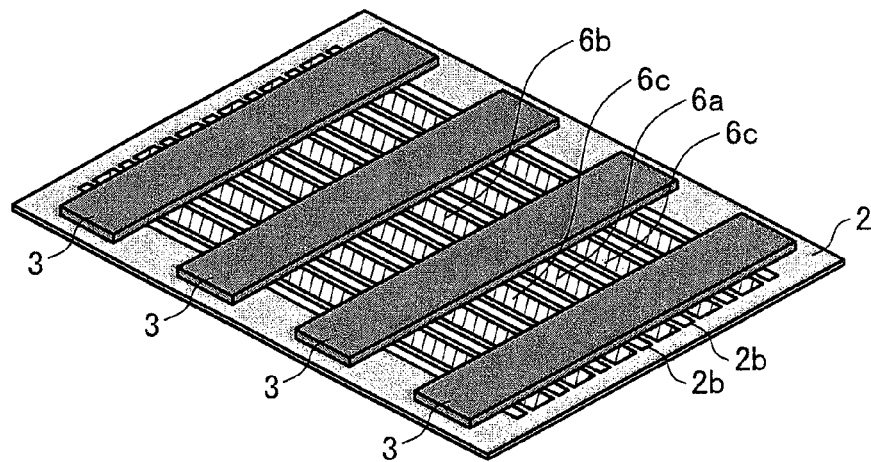
Figure 8:
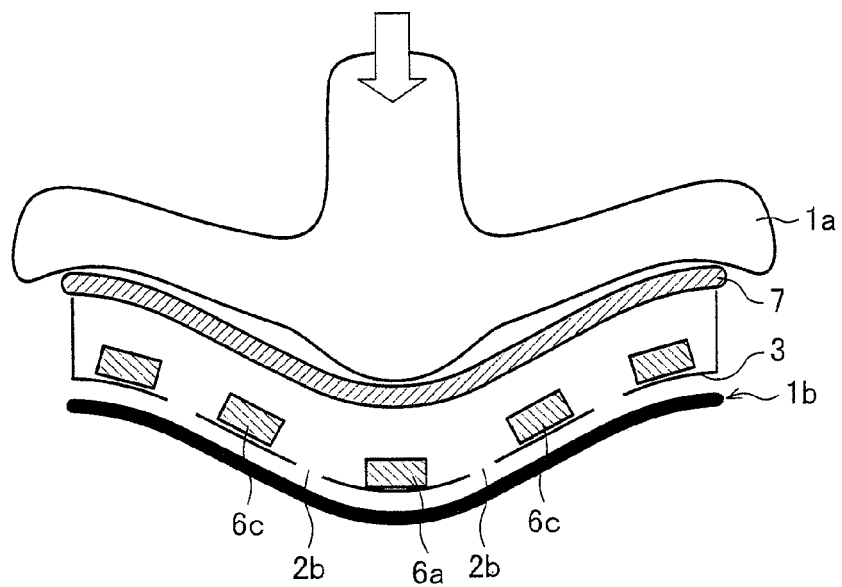

FIGS. 7(a) and 7(b) are diagrams illustrating capacitance elements. FIG. 7 (a) is an exploded perspective view illustrating capacitance elements in a conventional array type capacitance sensor. FIG. 7 (b) is a sectional view illustrating the capacitance elements of the conventional array type capacitance sensor which capacitance elements are observed in a case where the conventional array type capacitance sensor is positioned on a surface 1b to be detected. FIG. 8 (a) is an exploded perspective view illustrating capacitance elements in the array type capacitance sensor 1 of the present embodiment. FIG. 8 (b) is a sectional view illustrating the capacitance elements of the array type capacitance sensor 1 of the present embodiment which capacitance elements are observed in a case where the array type capacitance sensor 1 is positioned on the surface 1b to be detected. FIGS. 7 (a) and 8 (a) show movable electrodes 6a, 6b, and 6c. The movable electrodes 6a and 6b are adjacent to each other in the direction (direction indicated by arrow X in FIGS. 7 (a) and 8 (a)) in which the artery extends. The movable electrodes 6a and 6c are adjacent to one another in the direction (direction indicated by arrow Y in FIGS. 7 (a) and 8 (a)) orthogonal to the X direction. Capacitance elements (not shown) corresponding to the movable electrodes 6a, 6b, and 6c, are referred to as capacitance elements a, b, and c, respectively.

In a case where a person to be tested wears, on the wrist, a conventional array type capacitance sensor 1 while pressing the array type capacitance sensor 1 against the wrist, a plurality of strip-shaped electrodes are deformed so as to have a shape similar to outline of the surface (wrist) 1b to be detected. This is because the strip-shaped electrodes are provided on a single continuous movable-electrode-side substrate 2. Specifically, as illustrated in FIG. 7 (b), with regard to the capacitance element a lying at a portion of the array type capacitance sensor which portion is in contact with a concave portion of the wrist, a movable electrode 6a is under tensile stress caused by its adjacent movable electrodes 6c, whereas a fixed electrode 7a is under compressive stress. This causes a reduction in the distance between the movable electrode 6a and the fixed electrode 7a, thereby causing a change in the capacitance of the capacitance element a. This causes an increase in an initial output, as compared to (i) a normal state in which the conventional array type capacitance sensor 1 is not worn on the wrist, or (ii) a state in which the conventional array type capacitance sensor 1 is worn on a flat surface. Due to the above stresses constantly exerted on the electrodes during measurement, the change in capacitance, caused by the pressure (pulse pressure) from the surface (wrist) 1b to be detected, becomes small. In other words, the response of the capacitance element a becomes deteriorated, and consequently the sensitivity of the conventional array type capacitance sensor 1 is deteriorated. As described above, according to the conventional array type capacitance sensor, the capacitance element a, which receives pulse pressure, is affected by the adjacent capacitance elements c. This prevents precise and stable measurement of pressure.

In contrast, according to the array type capacitance sensor 1 of the present embodiment, the linear slits 2b are secured between adjacent ones of the strip-shaped electrodes on the movable-electrode-side substrate 2. In addition, the array type capacitance sensor 1 is attached to a wrist of a person to be tested such that the longitudinal direction of the slits 2b substantially matches the direction (direction indicated by arrow X in FIG. 8 (a)) in which an artery of the person to be tested extends. This causes the plurality of individual movable electrodes 6 to be deformed independently of one another so as to have a shape similar to the concavoconvexity of the wrist. Specifically, as illustrated in FIG. 8 (b), with respect to the capacitance element a lying at a portion of the array type capacitance sensor 1 which portion is pressed by the air bag 1a, the movable electrode 6a is separated from the adjacent movable electrodes 6c so as to be independent of the movable electrodes 6c. Thus, tensile stress is not caused by the movable electrodes 6c to the movable electrode 6a. Therefore, even in a case where the array type capacitance sensor 1 is worn on a concavoconvex surface, the relationship between the capacitance element a and the capacitance elements c is identical to a relationship obtained in a case where the array type capacitance sensor 1 is worn on a flat surface, i.e., is identical to the relationship between the capacitance element a and the capacitance element b. In other words, even when the array type capacitance sensor 1 is worn on a concavoconvex surface such as a bent surface or a curved surface, the array type capacitance sensor 1 merely has an apparent deformation. However, the states of the capacitance elements a, b, and c are the same as those shown when the array type capacitance sensor 1 is not worn on a concavoconvex surface. Therefore, unlike the conventional art, there occurs no increase in an initial output. This allows precise and stable measurement of pressure.

Furthermore, even when the array type capacitance sensor 1 is worn on a concavoconvex surface as described above, the capacitance element a and the capacitance elements c adjacent to each other are not affected by each other when the deformation occurs in the movable-electrode-side substrate 2 and the movable electrodes 6. This allows a reduction in cross talk, as compared to the conventional array type capacitance sensor.

As described above, the array type capacitance sensor 1 of the present embodiment is arranged so as to be worn such that both of (i) the direction in which the movable electrodes 6 extend and (ii) the direction in which the slits 2b extend substantially match the direction in which the artery of the person to be tested extends. In other words, the slits 2b are provided so as to be in a direction at right angles to the bend direction of the movable-electrode-side substrate 2 when the array type capacitance sensor 1 is worn. The bend direction refers to a direction in which the array type capacitance sensor 1 is bent when it is worn on the wrist of the person to be checked. In other words, the bend direction refers to a direction substantially at right angles to the direction in which the artery extends. As described above, the array type capacitance sensor 1 is worn such that the slits 2b between their adjacent movable electrodes 6 extend in the direction at right angles to the bend direction. This allows an increase in the effect of the slits 2b, i.e., the effect of causing the movable electrodes 6 to be deformed independently of one another.

The arrangement of the array type capacitance sensor 1 is not limited to the above. The array type capacitance sensor 1 can, for example, be arranged so as to be worn such that both the movable electrodes 6 and the slits 2b extend substantially at right angles to a direction in which the artery of the person to be checked extends. Even with this arrangement, the movable electrode 6a and the movable electrodes 6c are not affected by each other when the movable electrodes 6 are deformed. This is because a slit 2b is provided between a movable electrode 6a and a movable electrode 6c adjacent to each other. As a result, unlike the conventional art, an increase in an initial output is not caused. This allows precise and stable measurement of pressure.

As described above, an array type capacitance sensor 1 of the present embodiment is preferably arranged such that a plurality of capacitance elements are capable of being deformed independently of one another. Specifically, between adjacent ones of the capacitance elements, the slits 2b are preferably provided on the movable electrodes 6 side, or the spacer 3 is preferably provided.

[Result of Experiment]

Figure 9:
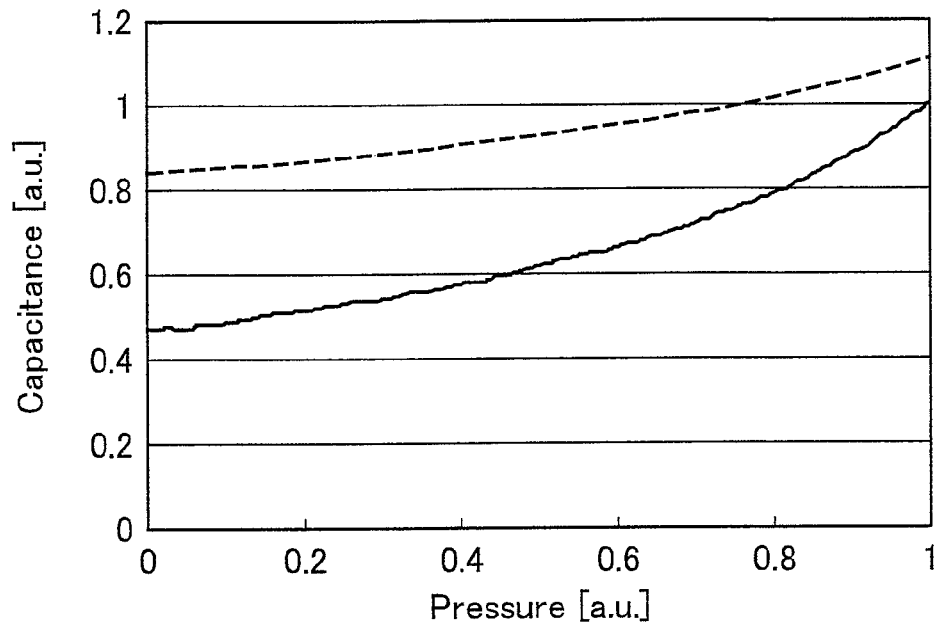
FIG. 9 (a) is a graph showing the relationship between pressure and capacitance in a conventional array type capacitance sensor.
Figure 9:
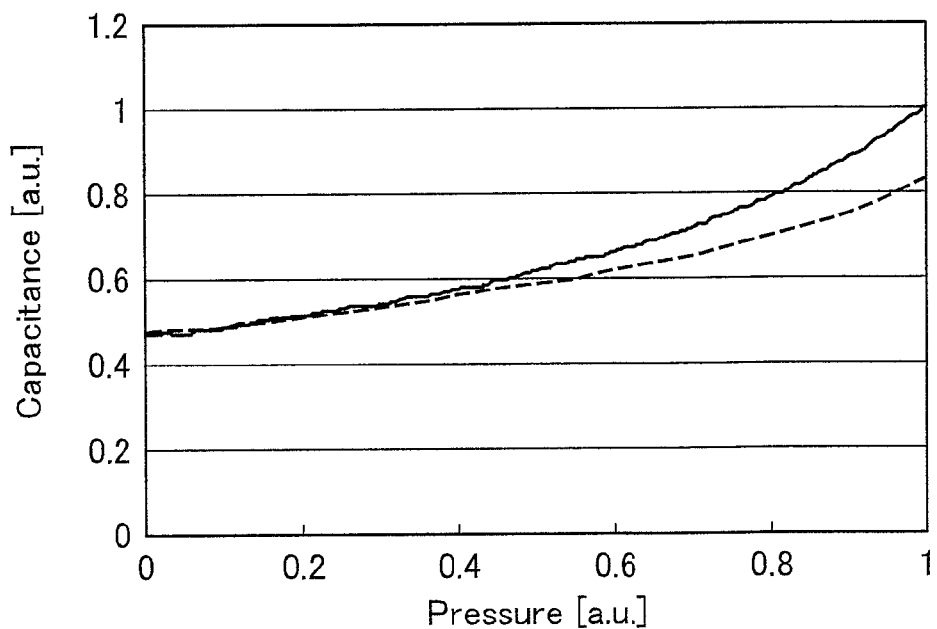

The following description deals with an experimental result demonstrating the effect described above. In this experiment, a measurement was made as to how the capacitance of a specific one of the capacitance elements changed when the pressure is applied to the entire array type capacitance sensor 1. FIG. 9 (*a*) is a graph showing the relationship between pressure and capacitance in a conventional array type capacitance sensor. FIG. 9 (*b*) is a graph showing the relationship between pressure and capacitance in the array type capacitance sensor 1 of the present embodiment in which the slits 2b are provided on the movable-electrode-side substrate 2. In FIG. 9 (*a*), the dotted line shows the result of measurement made when the conventional array type capacitance sensor was attached onto a flat surface (in case of a flat state), whereas the dotted line in FIG. 9 (*b*) shows the result of measurement made when the array type capacitance sensor 1 was attached onto a flat surface. In FIG. 9 (*a*), the solid line shows the result of measurement made when the conventional array type capacitance sensor was attached to an R10 fixture (a jig having a portion 10 mm in radius) (in case of a bent surface), whereas the solid line in FIG. 9 (*b*) shows the result of measurement made when the array type capacitance sensor 1 was attached onto an R10 fixture.

The conventional array type capacitance sensor and the array type capacitance sensor 1 used in the present experiment each satisfy the following design conditions: the movable-electrode-side substrate 2 includes 24 arranged movable electrodes 6, provided at intervals of 1 mm, each of which has a thickness of 125 μm, a width of 0.8 mm, and a length of 22 mm; the fixed-electrode-side substrate 5 includes three fixed electrodes 7, provided at intervals of 10 mm, each of which has a thickness of 125 μm, a width of 2 mm, and a length of 25 mm; the spacer 3 is made of polyester film having a thickness of 100 μm; and the dielectric film 4 is made of epoxy film having a thickness of 20 μm. The difference between the conventional array type capacitance sensor and the array type capacitance sensor 1 of the present embodiment reside in that the movable-electrode-side substrate 2 in the array type capacitance sensor 1 of the present embodiment includes 25 slits 2b, provided at intervals of 1 mm, each of which has a width of 0.2 mm.

With respect to the conventional array type capacitance sensor, as shown in FIG. 9 (*a*), it was confirmed that the initial output obtained in case of the flat surface was different from in case of the bent surface, and in particular, that the initial output increased in the bent state. This is because, as described above, merely attaching the array type capacitance sensor 1 onto a concavoconvex member causes the movable electrodes 6 and the fixed electrodes 7 to be under compressive stress or tensile stress, and ultimately causes the pressure to be applied to the capacitance elements. In addition, it was confirmed by changes in gradients of the lines that the tendencies to increase in the capacitances obtained in case of the flat surface and in case of the bent surface change, respectively, as the pressure to be applied increases. Specifically, it was confirmed that the gradient of the line obtained in the case of the bent surface is less sharp than that obtained in the case of the flat surface. This is considered to be due to the influence of the compressive stress and the tensile stress described above. In other words, the compressive stress and the tensile stress are both constantly applied to the capacitance elements. This causes the capacitances of the capacitance elements to change to a smaller degree in response to an increase in the pressure applied from a concavoconvex member. It was confirmed, as described above, that measurement results of the conventional array type capacitance sensor changed depending on the outline of a measuring object. As a result, it was confirmed that the conventional array type capacitance sensor was incapable of measuring pressure precisely and stably in cases where the movable electrodes 6 were deformed in response to the attachment of the conventional array type capacitance sensor to an object such as a concavoconvex member.

In contrast, according to the array type capacitance sensor 1 of the present embodiment, as shown in FIG. 9 (*b*), it was confirmed that the initial outputs obtained in the case of the flat and bent surfaces were not different from each other. In addition, it was confirmed by the gradients of the lines that the tendencies to increase in the capacitances obtained in the flat and bent surfaces are substantially identical as the level of pressure applied increases. In other words, it was confirmed that measurement results of the array type capacitance sensor 1 of the present embodiment did not change depending on the outline of a measuring object. As a result, it was confirmed, even in a case where the array type capacitance sensor 1 is attached to an object such as a concavoconvex member, that the array type capacitance sensor 1 of the present embodiment exhibited a characteristic identical to a characteristic exhibited when the array type capacitance sensor 1 was not attached to such an object, i.e., when the array type capacitance sensor 1 is in the flat state. It was therefore confirmed that the array type capacitance sensor 1 of the present embodiment was capable of measuring pressure precisely and stably even in cases where the movable electrodes 6 were deformed in response to the attachment of the array type capacitance sensor 1 to an object such as a concavoconvex member.

Figure 10:
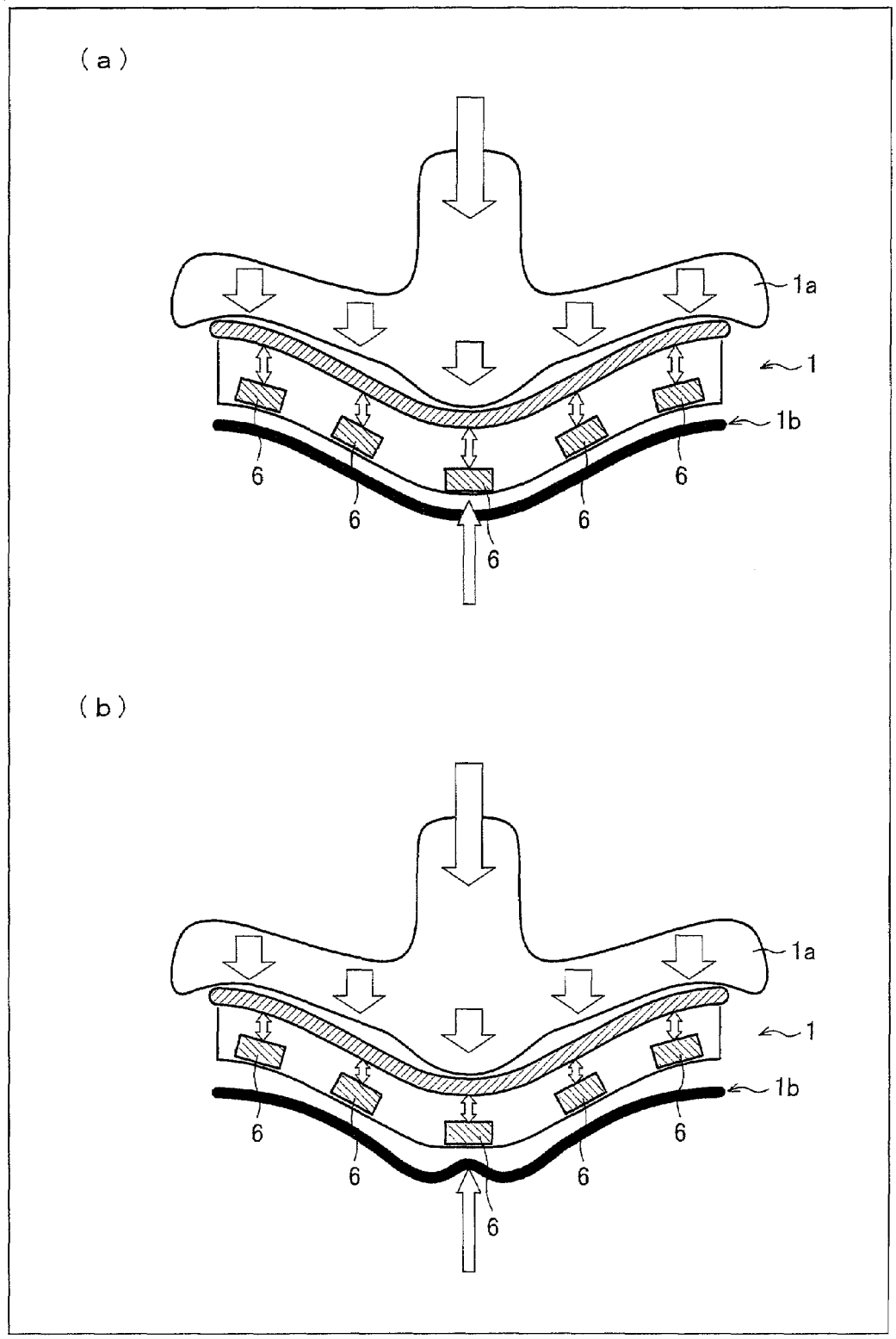
FIG. 10 is a cross-sectional view illustrating the capacitance elements observed in a case where the conventional array type capacitance sensor is attached to a detection surface, in which (a) and (b) illustrate how the movable electrodes are deformed when the pressure is applied to the conventional array type capacitance sensor.
Figure 11:
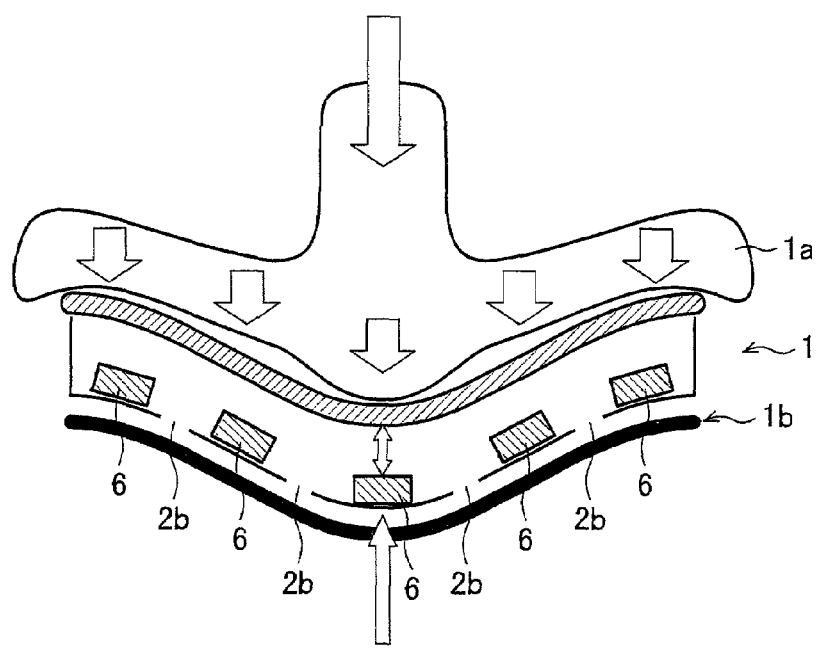
FIG. 11 is a cross-sectional view illustrating the capacitance elements observed in a case where the array type capacitance sensor of Embodiment 1 is attached to a detection surface, in which (a) and (b) illustrate how the movable electrodes are deformed when the pressure is applied to the array type capacitance sensor of Embodiment 1.
Figure 11:
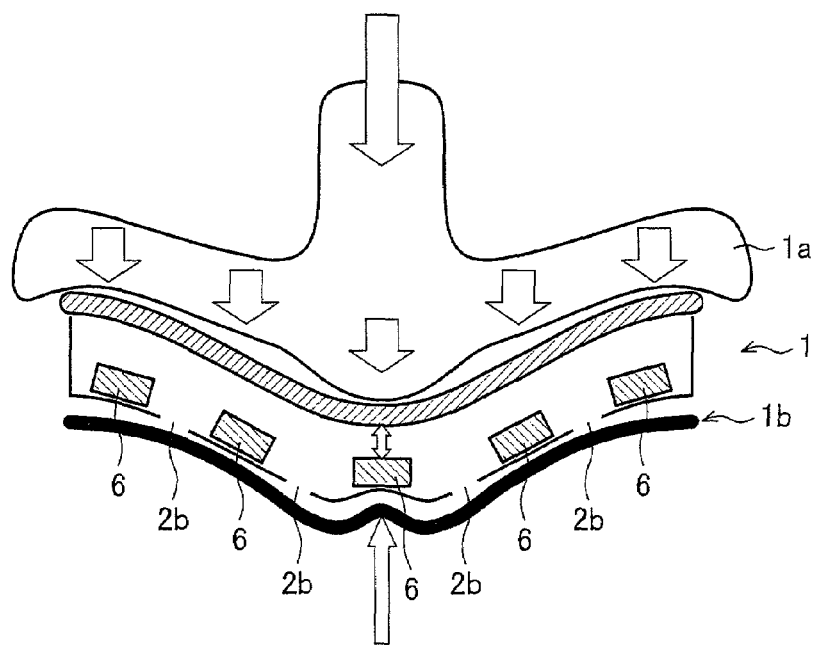
Figure 12:
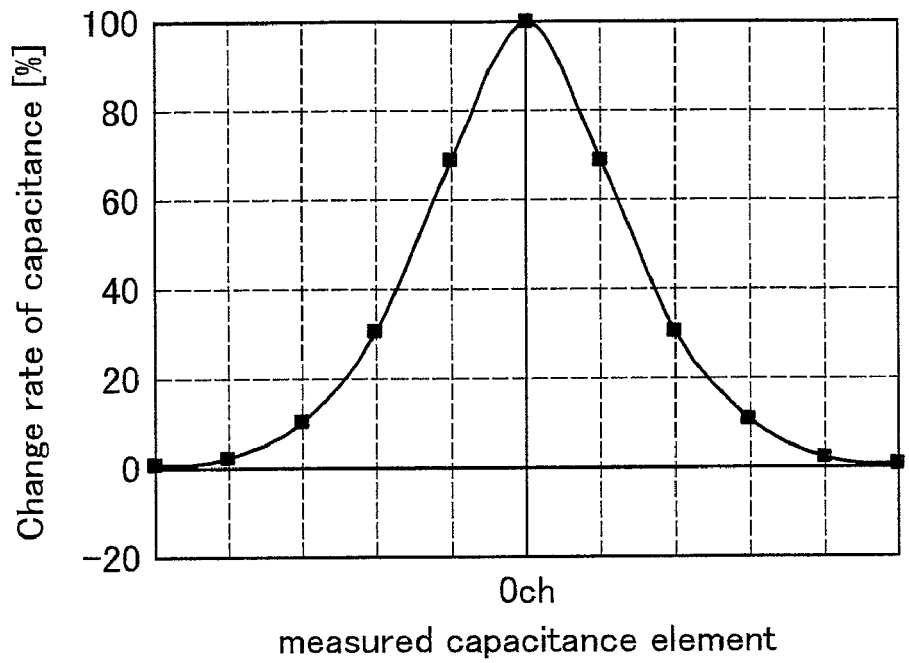
FIG. 12 is a graph showing how cross talk has occurred in the conventional array type capacitance sensor.
Figure 13:
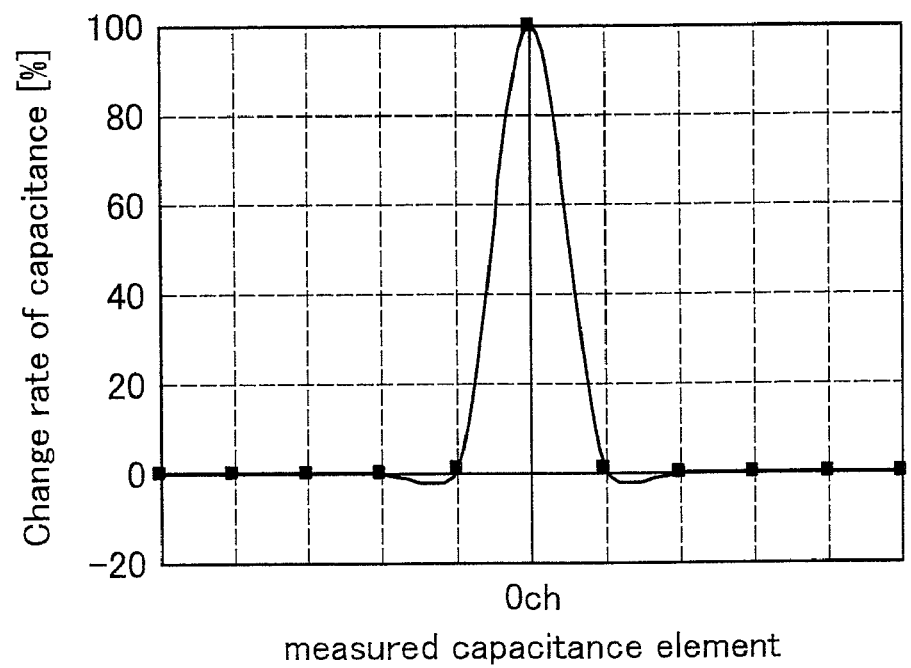
FIG. 13 is a graph showing how cross talk has occurred in the array type capacitance sensor of Embodiment 1.

The following description deals with an experimental result for verifying the foregoing cross talk occurring in each of the conventional array type capacitance sensor and the array type capacitance sensor 1 of the present embodiment. In this experiment, the array type capacitance sensor 1 was attached to an R-10 fixture similar to the R-10 fixture used in the foregoing experiment. While pressure was being applied to a specific one (0 ch) of the capacitance elements, measurement was made as to what was a ratio between a change in capacitances of capacitance elements surrounding the specific one (0 ch) of the capacitance elements and a change in capacitance of the specific one (0 ch) of the capacitance elements, respectively. FIG. 10 is a cross-sectional view illustrating the capacitance elements observed in a case where the conventional array type capacitance sensor is attached to a surface to be detected. In FIG. 10, (*a*) and (*b*) illustrate how the movable electrodes 6 are deformed when the pressure is applied to the conventional array type capacitance sensor. FIG. 12 is a graph showing how the capacitances in the conventional array type capacitance sensor have changed. FIG. 11 is a cross-sectional view illustrating the capacitance elements observed in a case where the array type capacitance sensor 1 of the present embodiment is attached to a surface to be detected. In FIG. 11, (*a*) and (*b*) illustrate how the movable electrodes 6 are deformed when the pressure is applied to the array type capacitance sensor 1. FIG. 13 is a graph showing how the capacitances in the array type capacitance sensor 1 have changed.

The movable electrodes 6 included in the conventional array type capacitance sensor are incapable of being deformed independently of one another, when the pressure is applied to the conventional array type capacitance sensor. This causes more than one of the movable electrodes 6 to be deformed as illustrated in (*a*) and (*b*) of FIG. 10. This is clear from the graph of FIG. 12 as well. It was then confirmed, in the conventional array type capacitance sensor, that the pressure applied to a specific one (0 ch) of the capacitance elements affected other capacitance elements, that is, large cross talk occurred. It was particularly made clear that about 70% of the pressure applied to a specific one of the capacitance elements is transmitted to the adjacent ones of the capacitance elements.

In contrast, the movable electrodes 6 included in the array type capacitance sensor 1 of the present embodiment are capable of being deformed independently of one another, when the pressure is applied to the array type capacitance sensor 1. This is due to the slits 2*b* provided in the movable-electrode-side substrate 2. In consequence, as illustrated in (*a*) and (*b*) of FIG. 11, deformed is only a specific one of the movable electrodes 6 whose location is in a deformed portion of a target surface 1*b* to be detected. As is clear from the graph of FIG. 13, it was confirmed that the pressure applied to a specific one (0 ch) of the capacitance elements did not affect other capacitance elements. Note that similar result was obtained with respect to any one of capacitance elements other than the specific capacitance element (0 ch). Thus, it was confirmed that the array type capacitance sensor 1 of the present embodiment was capable of reducing cross talk, as compared to the conventional array type capacitance sensor.

As is clear from the experimental results of FIGS. 12 and 13, it was confirmed that it was possible to (i) precisely and stably measure pressure, and (ii) reduce cross talk as compared to the conventional array type capacitance sensor, by the provision of the slits 2*b* in the movable-electrode-side substrate 2 including the movable electrodes 6 forming the capacitance elements.

Figure 14:
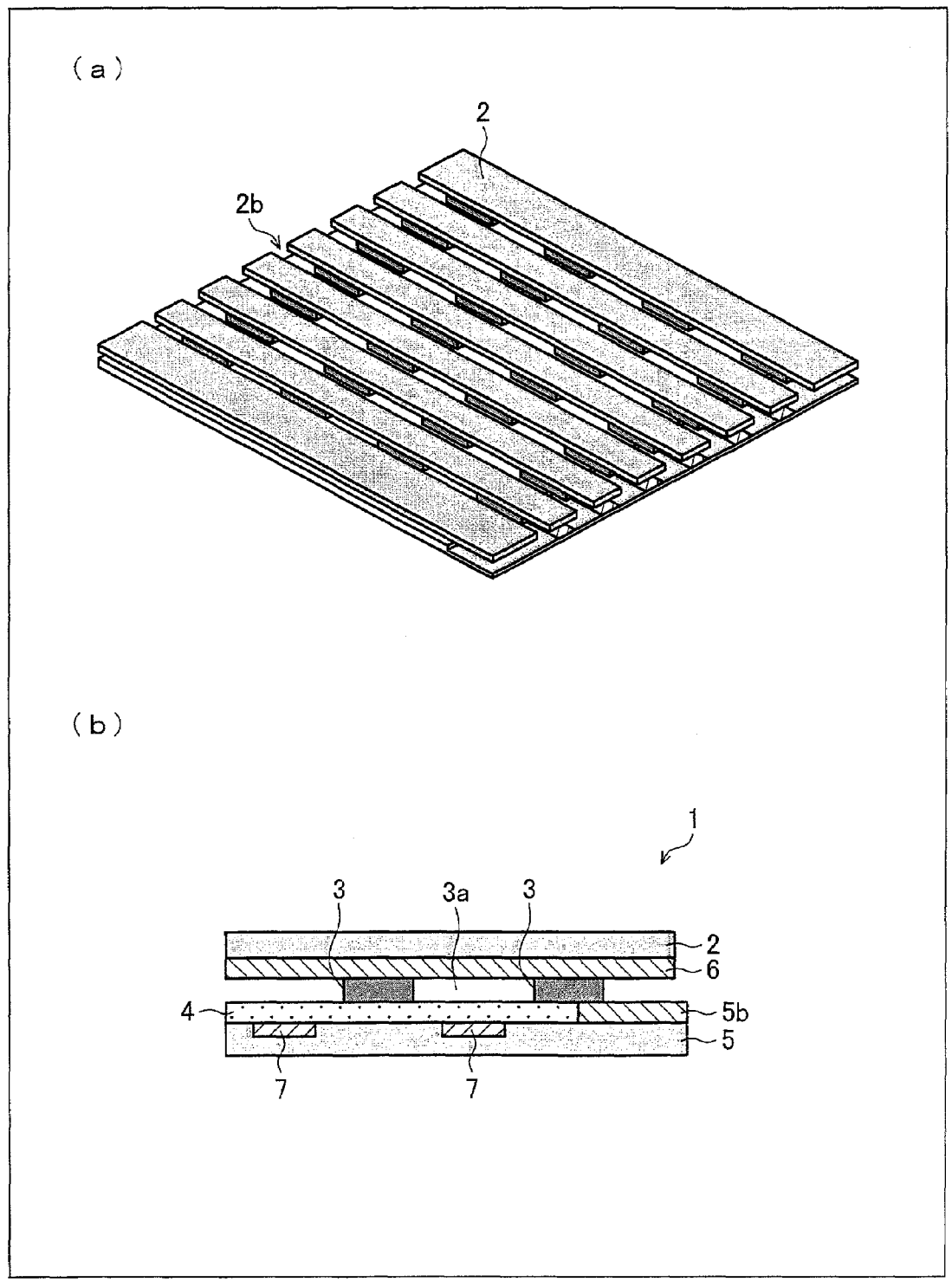
FIG. 14 is a view illustrating a schematic arrangement of the arrange type capacitance sensor of Embodiment 1, (a) shows a case in which the slits in the array type capacitance sensor are further extended toward both end parts of the movable-electrode-side substrate, and (b) is a sectional view of the arrange type capacitance sensor in which a conductive adhesive is used as the spacer.

As illustrated in (*a*) of FIG. 3, according to the present embodiment, the movable-electrode-side substrate 2 is provided with the slits 2*b* extending along the 24 rows of strip-shaped movable electrodes 6, and is arranged so that each of its both end parts is integrally provided. Alternatively, as illustrated in (*a*) of FIG. 14, the movable-electrode-side substrate 2 can, for example, be arranged such that slits 2*b* are provided so as to further extend toward both end parts of the movable-electrode-side substrate 2. This causes each of its both end parts to be not integrally provided but to be split off. With the alternative arrangement, it is possible for a movable-electrode-side substrate 2 to be provided with 24 independent movable electrodes 6. This allows an improvement in the above-mentioned effect of the slits 2*b*. Specifically, the alternative arrangement improves the flexibility of the movable electrodes 6, and therefore it is possible to measure pressure with higher precision. In addition, since adjacent ones of the movable electrodes 6 are completely separated from each other, it is possible to further reduce cross talk. In the above arrangement, it is preferable to use a conductive adhesive as the spacer 3 as illustrated in (*b*) of FIG. 14. This allows a wiring pattern on the movable electrode 6 side to be drawn out and extended to the fixed electrode 7 side, by using a wire 5*b* on the fixed-electrode-side substrate 5.

EMBODIMENT 2

Figure 15:
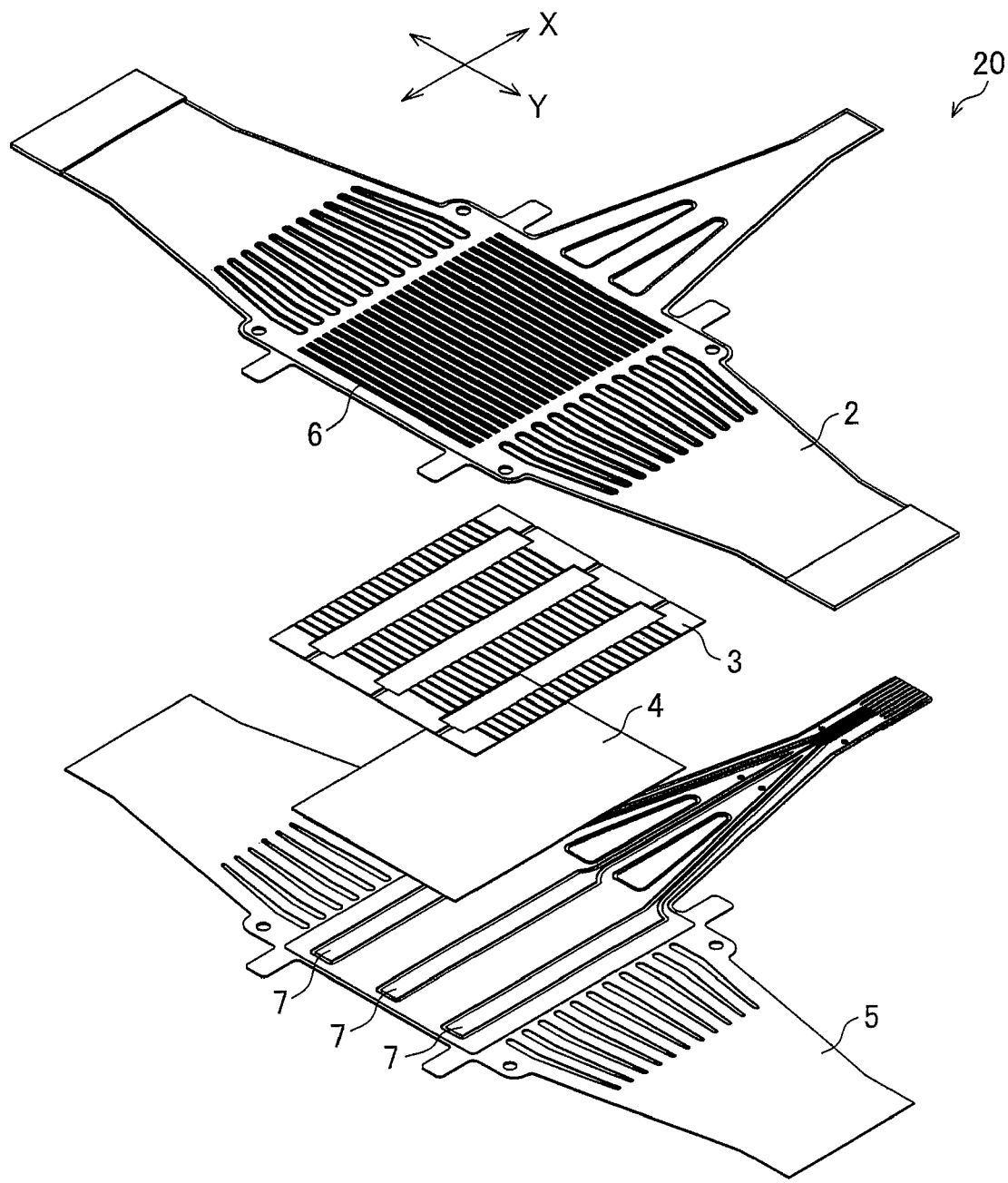
FIG. 15 is an exploded perspective view of an array type capacitance sensor in accordance with Embodiment 2 of the present invention.
Figure 16:
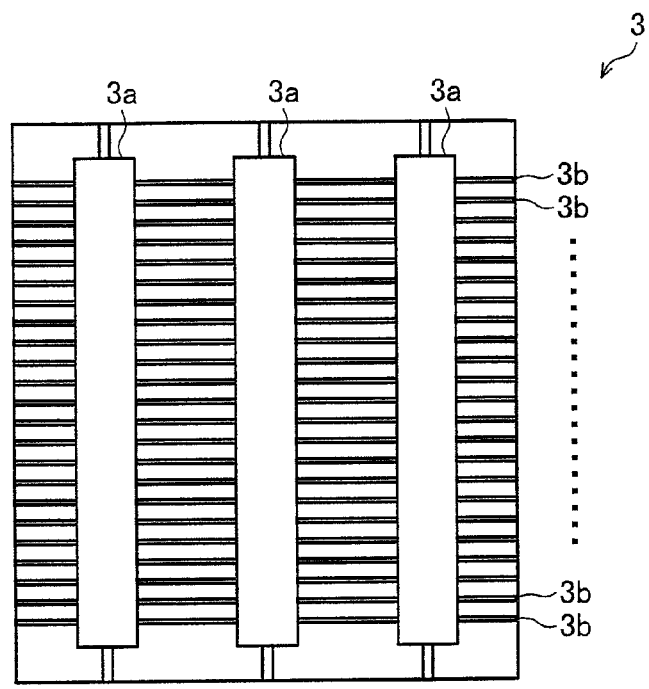
FIG. 16 is a view schematically illustrating how a spacer is arranged in Embodiment 2, in which (a) is a plan view of the spacer, and (b) is a perspective view of the spacer.
Figure 16:
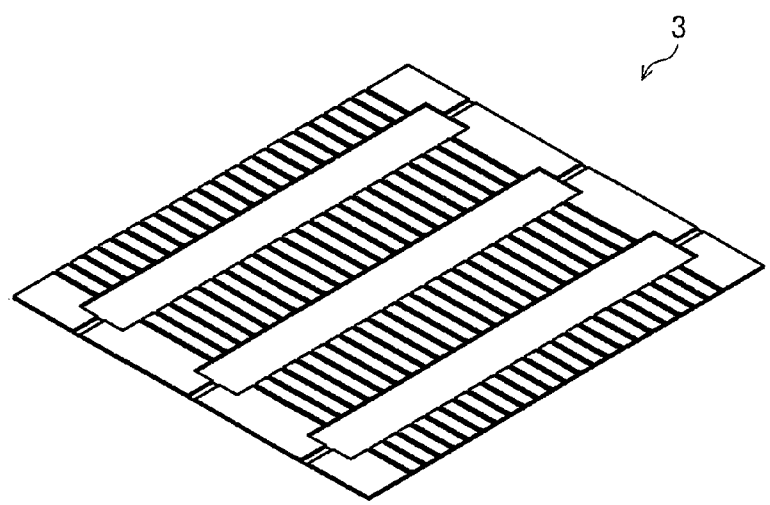

The following description deals with Embodiment 2 of the present invention with reference to FIGS. 15 and 16. It should be noted that, for convenience of explanation, same members in Embodiment 2 as those in Embodiment 1 are assigned the same reference numerals and the description of the members is omitted.

FIG. 15 is an exploded perspective view of an array type capacitance sensor 20 according to Embodiment 2 of the present invention. The array type capacitance sensor 20 of the present embodiment is different from the array type capacitance sensor 1 of Embodiment 1 in that the spacer 3 is improved.

FIG. 16 is a view schematically illustrating how a spacer 3 is arranged in the present embodiment. In FIG. 16, (*a*) is a plan view of the spacer 3, and (*b*) is a perspective view of the spacer 3. As illustrated in FIG. 16, the spacer 3 is provided with opening sections 3*a* for the three columns of fixed electrodes 7 so as not to cover the fixed electrodes 7 on the fixed electrode side substrate 5 when the spacer 3 is stacked and combined. In addition, the spacer 3 is provided with slits (spacer slit sections) 3*b* which are located in the same positions in their thickness direction as the slits 2*b* in the movable-electrode-side substrate 2, respectively, so as to coincide with the slits 2*b*.

With the arrangement, in a case where the array type capacitance sensor 20 is attached to a concavoconvex member, the movable electrodes 6 are deformed more easily than the movable electrodes 6 of Embodiment 1 so as to have a shape similar to the outline of the concavoconvex surface. In this case as well, the movable electrodes 6 are capable of being deformed independently of one another. As such, capacitance elements corresponding to a deformed portion of the array type capacitance sensor 20 is not under compressive stress or tensile stress. The array type capacitance sensor 20 of the present embodiment improves the flexibility of the movable electrodes 6, as compared with the array type capacitance sensor 1 of Embodiment 1. This allows a change in pressure to be measured with higher precision, and allows a further reduction in cross talk.

In a case where the slits 2*b* in the movable-electrode-side substrate 2 are extended so as to completely separate the individual strip-shaped movable electrodes 6 from one another as in Embodiment 1, the above-mentioned effect can be enhanced further.

EMBODIMENT 3

Figure 17:
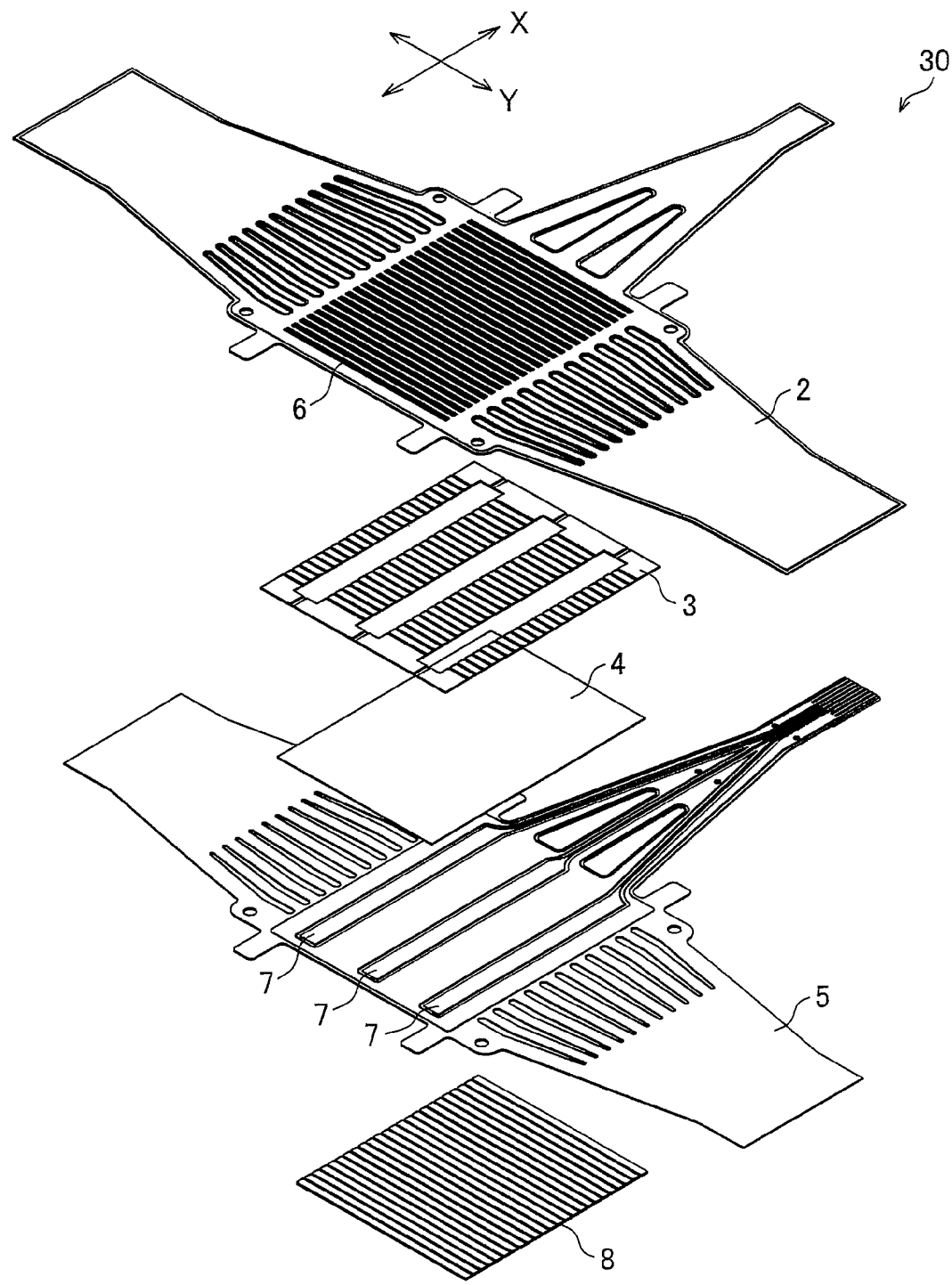
FIG. 17 is an exploded perspective view of an array type capacitance sensor according to Embodiment 3 of the present invention.
Figure 18:
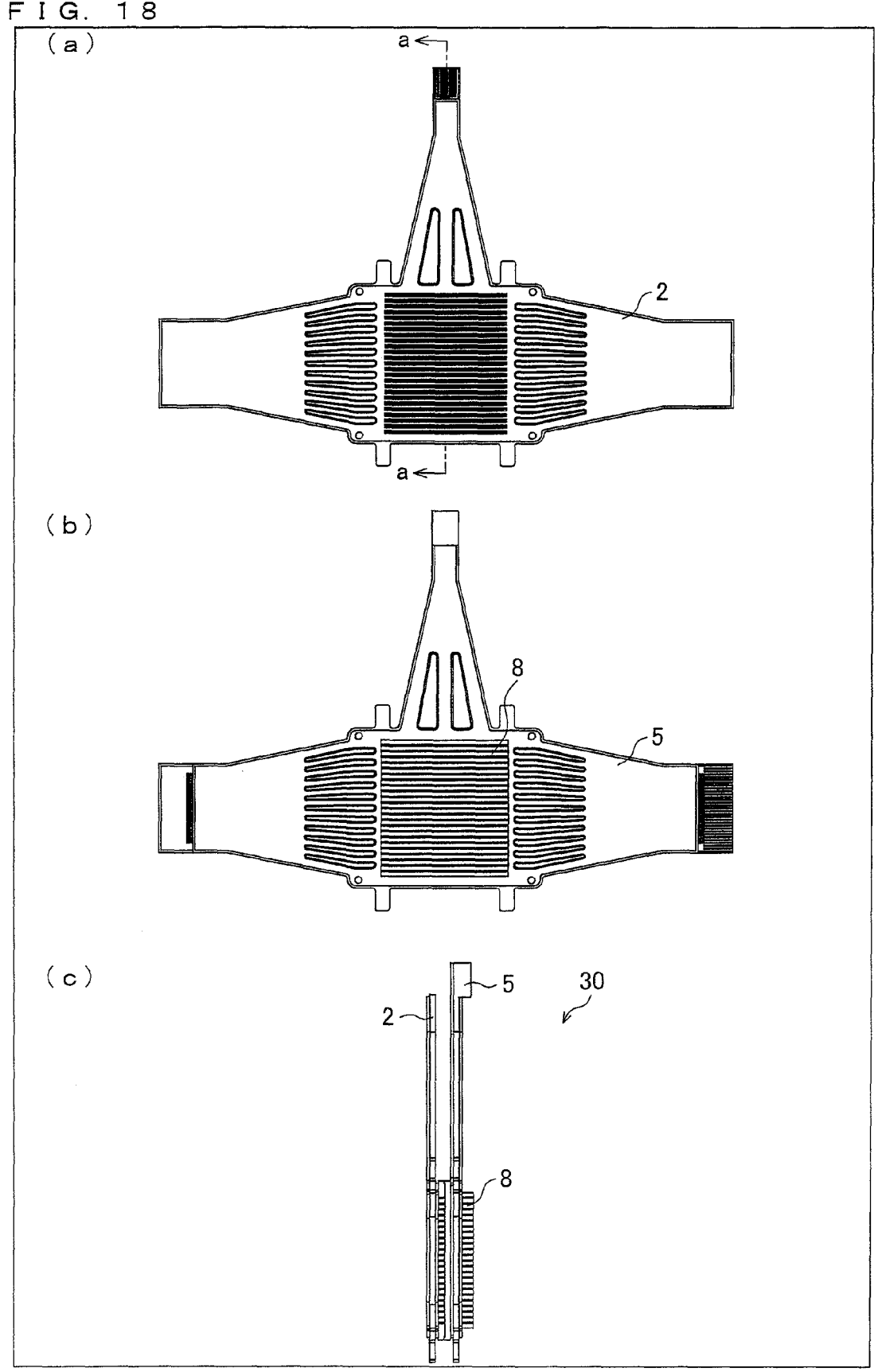
FIG. 18 is a view schematically illustrating an arrangement of the array type capacitance sensor of Embodiment 3, (a) is a top plan view of the movable-electrode-side substrate of the array type capacitance sensor, (b) is a bottom plan view of the fixed-electrode-side substrate of the array type capacitance sensor, and (c) is a cross-sectional view of the array type capacitance sensor, taken along the line a-a shown in (a).
Figure 19:
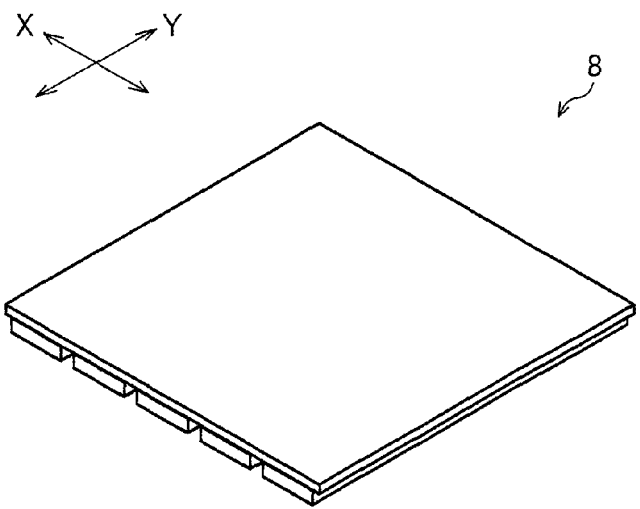
FIG. 19 is a view schematically illustrating an arrangement of the stabilizing member of Embodiment 3, (a) is a perspective view of the stabilizing member, and (b) is a side view obtained when the stabilizing member illustrated in (a) is viewed in the Y direction.
Figure 19:
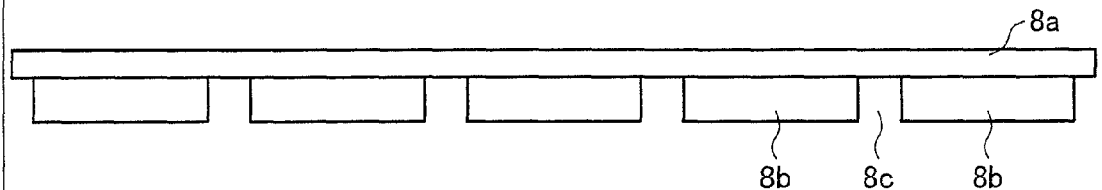

The following description deals with Embodiment 3 of the present invention with reference to FIGS. 17 through 19. It should be noted that, for convenience of explanation, same members in Embodiments 3 as those in Embodiments 1 and 2 are assigned the same reference numerals and the description of the members is omitted.

FIG. 17 is an exploded perspective view of an array type capacitance sensor 30 according to Embodiment 3 of the present invention. FIG. 18 is a view schematically illustrating an arrangement of the array type capacitance sensor 30 of the present embodiment, (*a*) is a top plan view of the movable-electrode-side substrate 2 of the array type capacitance sensor 30, (*b*) is a bottom plan view of the fixed-electrode-side substrate 5 of the array type capacitance sensor 30, and (*c*) is a cross-sectional view of the array type capacitance sensor 30, taken along the line a-a shown in (*a*). The array type capacitance sensor 30 of the present embodiment further includes a stabilizing member 8, as compared with the arrangement of the array type capacitance sensor 20 of Embodiment 2.

FIG. 19 is a view schematically illustrating an arrangement of the stabilizing member 8 of the present embodiment. In FIG. 19, (*a*) is a perspective view of the stabilizing member 8, and (*b*) is a side view obtained when the stabilizing member 8 illustrated in (*a*) is viewed in the Y direction. As illustrated in FIG. 19, the stabilizing member 8 is provided with a plurality of grooves. Specifically, the stabilizing member 8 includes: a single thin film plate (e.g., an adhesive sheet) 8*a*; and a plurality of protrusion plates 8*b* on the thin film plate 8*a*. The protrusion plates 8*b* are provided at equal spaces so as to linearly extend in parallel with one another. It should be noted that, although (*a*) and (*b*) of FIG. 19 each show, for convenience of explanation, a case in which only five protrusion plates 8*b* are provided, the number of the protrusion plates 8*b* is preferably the same as the number of the movable electrodes 6 (i.e., 24 in this embodiment) on the movable-electrode-side substrate 2. In addition, a gap between adjacent ones of the protrusion plates 8*b*, i.e., a groove 8*c*, has a width which is set so that adjacent ones of the protrusion plates 8*b* do not buffer each other when the stabilizing member 8 is deformed. Further, it is preferable that a short-side width of each of the protrusion plates 8*b* be substantially the same as a short-side width of each of the movable electrodes 6.

The stabilizing member 8 is provided, on a surface of the fixed-electrode-side substrate 5 which surface is on the opposite side of a surface on which the fixed electrodes 7 are provided, such that the projection positions of (i) the plurality of movable electrodes 6 and (ii) the plurality of protrusion plates 8*b* coincide with each other. In consequence, the slits 2*b* in the movable-electrode-side substrate 2, the slits 3*b* in the spacer 3, and the grooves 8*c* in the stabilizing member 8 coincide, in their positions, with one another in their thickness direction.

With the arrangement, in a case where the array type capacitance sensor 30 is attached to a concavoconvex member, the movable electrodes 6 are bent from the slits 2*b* and 3*b* and the grooves 8*c*, respectively. As such, it is possible to maintain the flexibility of the array type capacitance sensor 30, and to ensure the planarity of the movable electrodes 6 and the fixed electrodes 7, both of which constitute the capacitance elements. As a result, the array type capacitance sensor 30 of the present embodiment is capable of measuring a change in pressure with higher precision and reducing more cross talk than the array type capacitance sensor 1 of Embodiment 1 and the array type capacitance sensor 20 of Embodiment 2.

As in Embodiment 2, the slits 2*b* in the movable-electrode-side substrate 2 may be extended to separate the individual strip-shaped movable electrodes 6 from one another so that the movable electrodes 6 are completely separated from one another.

Figure 20:
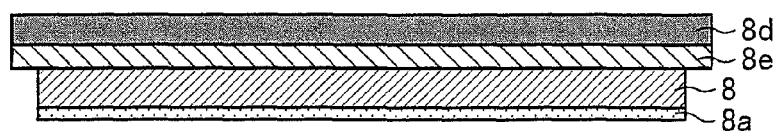
FIG. 20 is a view illustrating steps for attaching the stabilizing member of Embodiment 3 to the fixed-electrode-side substrate.
Figure 20:
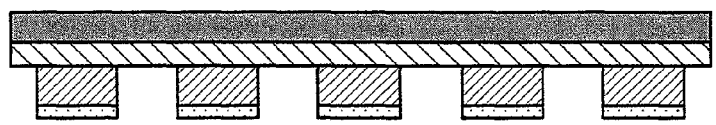
Figure 20:
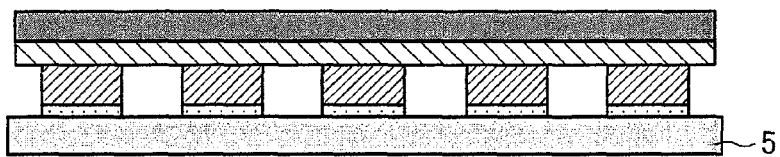
Figure 20:
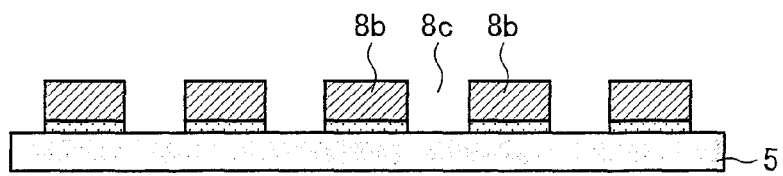

With reference to FIG. 20, the following description deals with an exemplary method for attaching the stabilizing member 8 to the fixed-electrode-side substrate 5. In FIG. 20, (*a*) through (*d*) illustrate steps for attaching the stabilizing member 8 to the fixed-electrode-side substrate 5. First, provisional contact bonding of an adhesive sheet 8*a* is carried out with respect to the stabilizing member 8, while the stabilizing member 8 is being brought into close contact with a release sheet including a PET film 8*d* and a release member 8*e* ((*a*) of FIG. 20). Next, the stabilizing member 8 is cut by press working (half cut) ((*b*) of FIG. 20), and is then placed on the fixed-electrode-side substrate 5. The adhesive sheet 8*a* is subjected to thermo compression bonding ((*c*) of FIG. 20). After that, the release sheet is removed ((*d*) of FIG. 20), whereby the attachment of the stabilizing member 8 is complete.

EMBODIMENT 4

Figure 21:
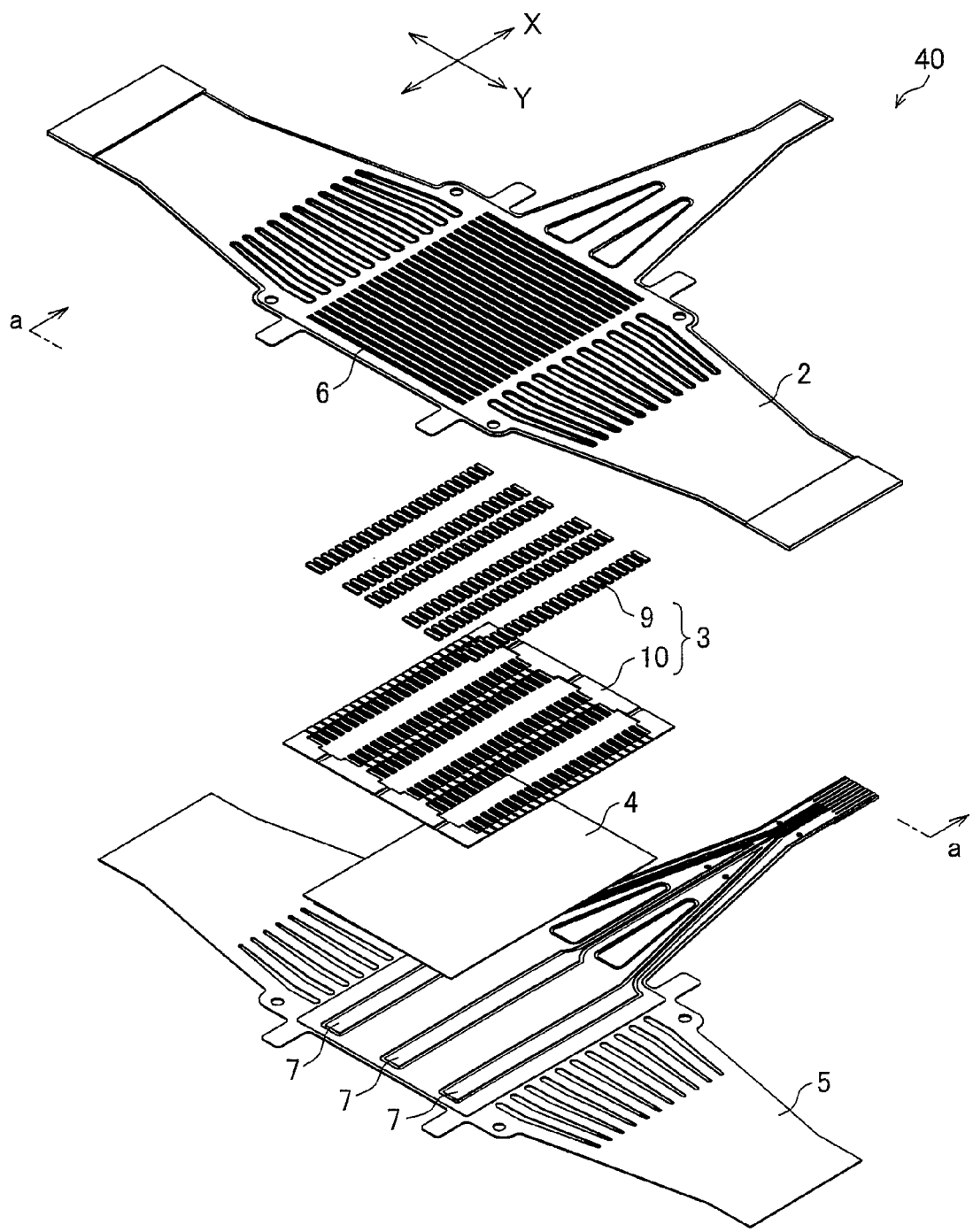
FIG. 21 is an exploded perspective view of an array type capacitance sensor in accordance with Embodiment 4 of the present invention.
Figure 22:
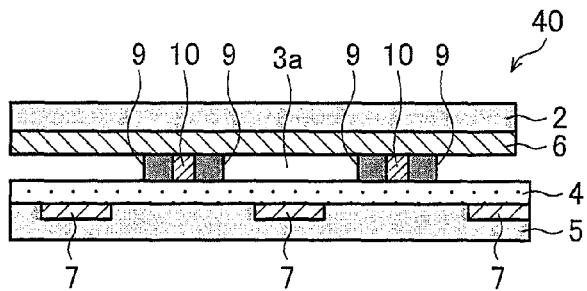
FIG. 22 is a partial sectional view of the array type capacitance sensor of Embodiment 4, taken along the line a-a of FIG. 21.
Figure 23:
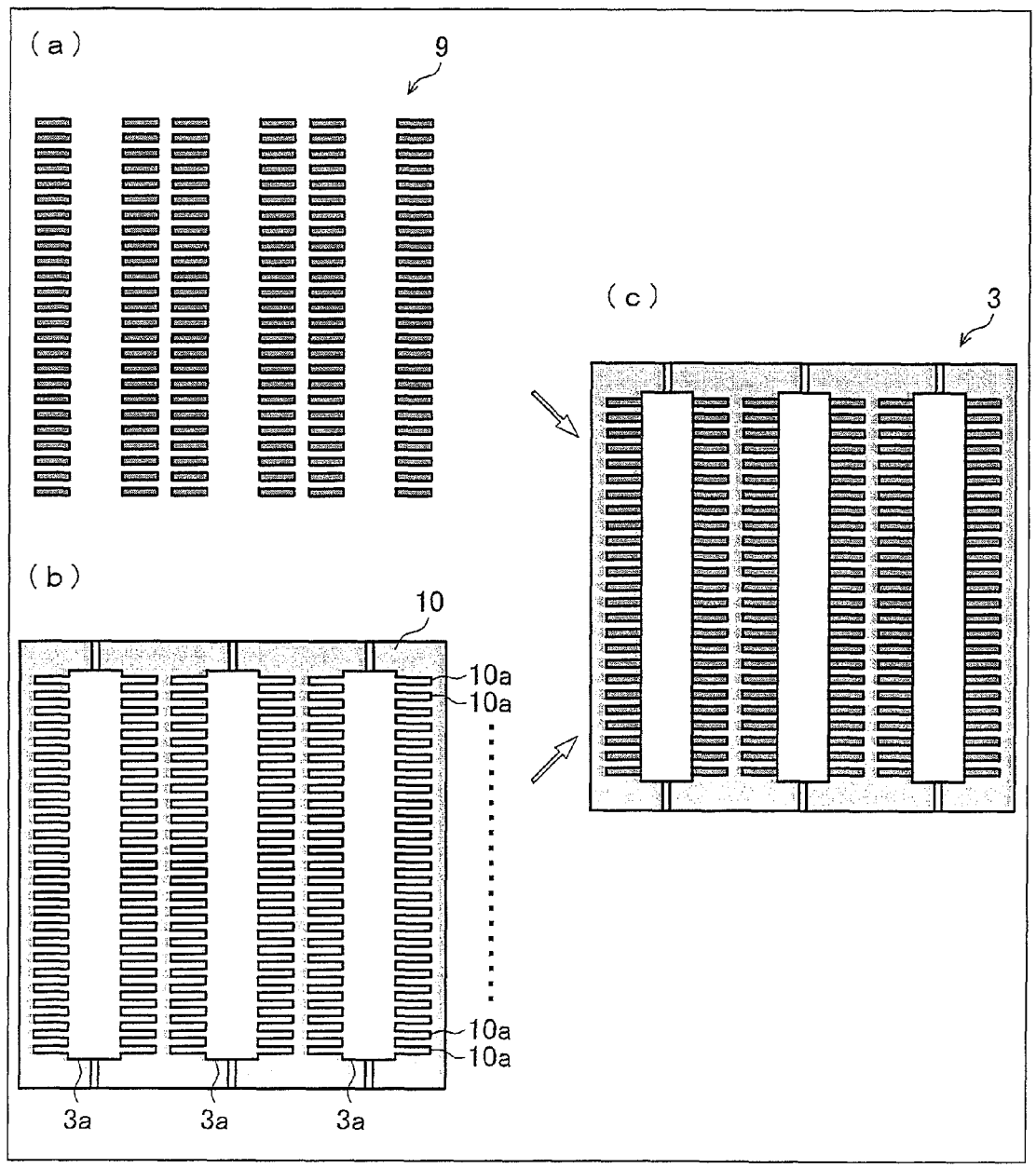
FIG. 23 is a view of respective schematic arrangements of constituent members of the array type capacitance sensor of Embodiment 4, in which (a) is a plan view of a gap stabilizing member, (b) is a plan view of an adhesive sheet, and (c) is a plan view of a spacer.

The following description deals with Embodiment 4 of the present invention with reference to FIGS. 21 through 23. It should be noted that, for convenience of explanation, same members in Embodiment 4 as those in Embodiments 1 through 3 are assigned the same reference numerals and the description of the members is omitted.

FIG. 21 is an exploded perspective view of an array type capacitance sensor 40 according to Embodiment 4 of the present invention. FIG. 22 is a partial sectional view of the array type capacitance sensor 40, taken along the line a-a of FIG. 21. The array type capacitance sensor 40 of the present embodiment is different from the array type capacitance sensor 20 of Embodiment 2 in that the spacer 3 is further improved.

(*c*) of FIG. 23 is a plan view of a schematic arrangement of a spacer 3 of the present embodiment. As illustrated in FIG. 23, the spacer 3 includes a gap stabilizing member 9 and an adhesive sheet 10. (*a*) of FIG. 23 is a plan view of a schematic arrangement of the gap stabilizing member 9. (*b*) of FIG. 23 is a plan view of a schematic arrangement of the adhesive sheet 10.

The gap stabilizing member 9 has flexibility and compressive strength which are equivalent to those of the movable-electrode-side substrate 2 and the fixed-electrode-side substrate 5. Specifically, the gap stabilizing member 9 is made of polyimide, PET (film), epoxy resin (film) or the like, for example.

As in the spacer 3 of Embodiment 2, the adhesive sheet 10 is provided with (i) opening sections 3*a* corresponding to the fixed electrodes 7 and (ii) slits 3*b* corresponding to the slits 2*b* separating the movable electrodes 6 from one another. In addition, as illustrated in (*b*) of FIG. 23, the adhesive sheet 10 is further provided with a plurality of cutouts 10*a* into which the gap stabilizing member 9 is to be fitted. The cutouts 10*a* are provided so as to be juxtaposed at even intervals and linearly extend in parallel with one another. Further, the cutouts 10*a* are provided so as to separate the individual slits (not shown) in the adhesive sheet 10 from one another. The cutouts 10*a* are positioned such that, when the spacer 3 is laminated to the movable-electrode-side substrate 2 and the fixed-electrode-side substrate 5, the respective projection positions of (i) the movable electrodes 6 on the movable-electrode-side substrate 2 and (ii) the cutouts 10*a* align with each other. The adhesive sheet 10 is made of polyester resin, epoxy resin, polyurethane resin, silicone resin or the like, for example.

Figure 24:
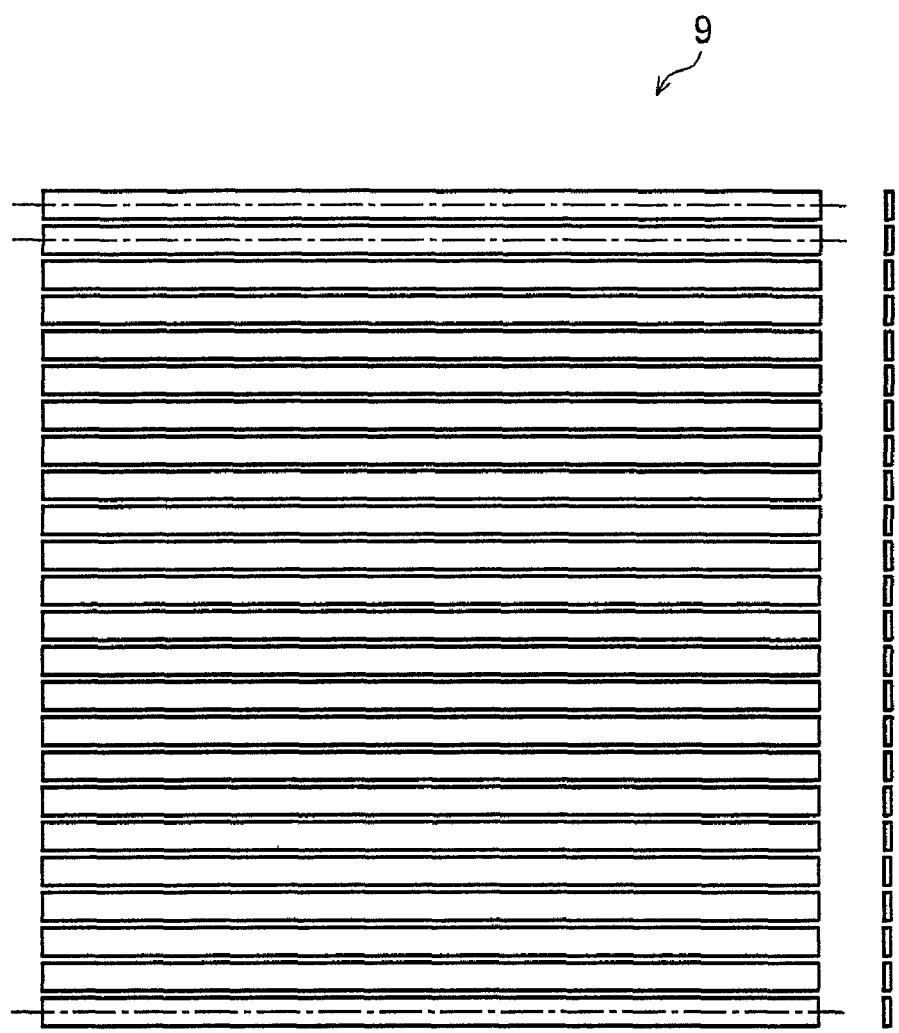
FIG. 24 is a view of a schematic arrangement of the gap stabilizing member of Embodiment 4 obtained before the gap stabilizing member is fitted into the adhesive sheet.

The following description deals with how the spacer 3, made up of the gap stabilizing member 9 and the adhesive sheet 10, is assembled. FIG. 24 is a view of a schematic arrangement of the gap stabilizing member 9 obtained before the gap stabilizing member 9 is fitted into the adhesive sheet 10. The gap stabilizing member 9 shown in FIG. 24 is processed in order to be fitted in the cutouts 10*a* in the adhesive sheet 10 (see (*a*) of FIG. 23). Then, the gap stabilizing member 9 and the adhesive sheet 10 are combined with each other as illustrated in (*c*) of FIG. 23.

Figure 25:
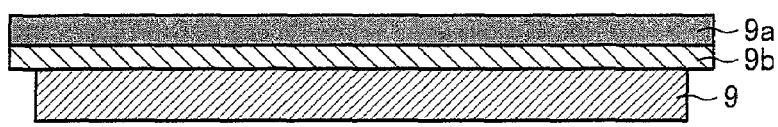
FIG. 25 is a view illustrating steps for assembling the spacer of Embodiment 4.
Figure 25:
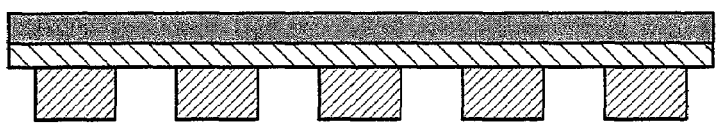
Figure 25:
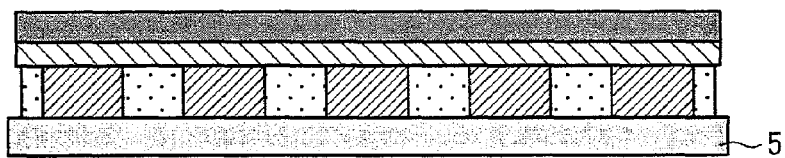
Figure 25:
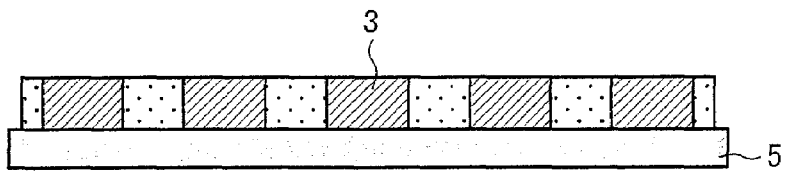
Figure 26:
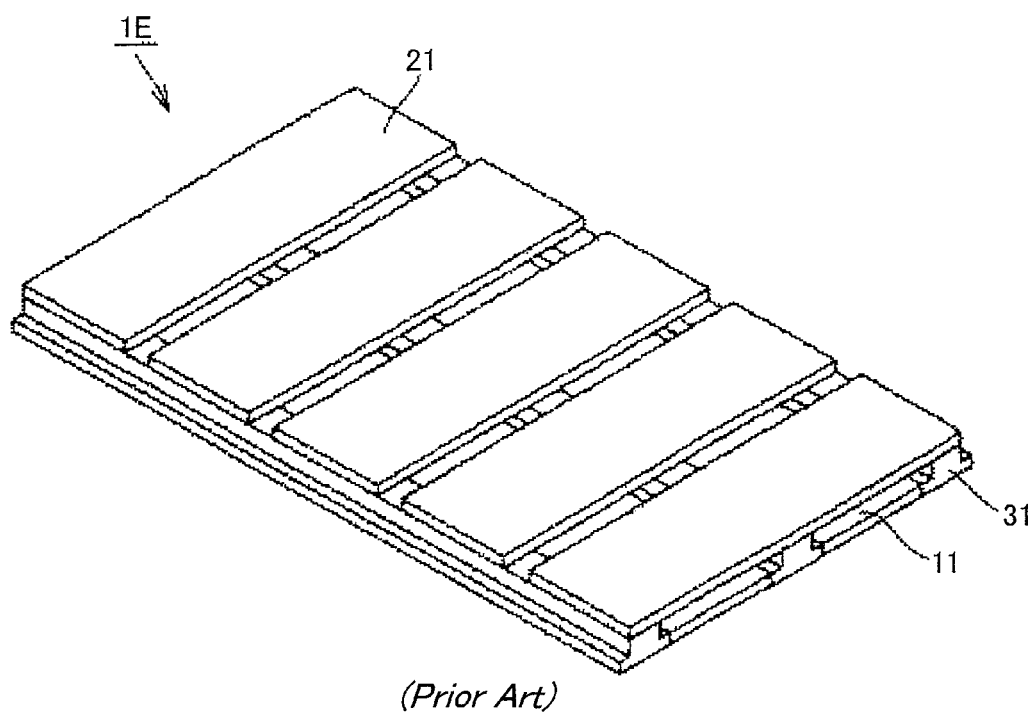
FIG. 26 is an outline perspective view of a pressure detection section included in a conventional capacitance pressure sensor.
Figure 27:
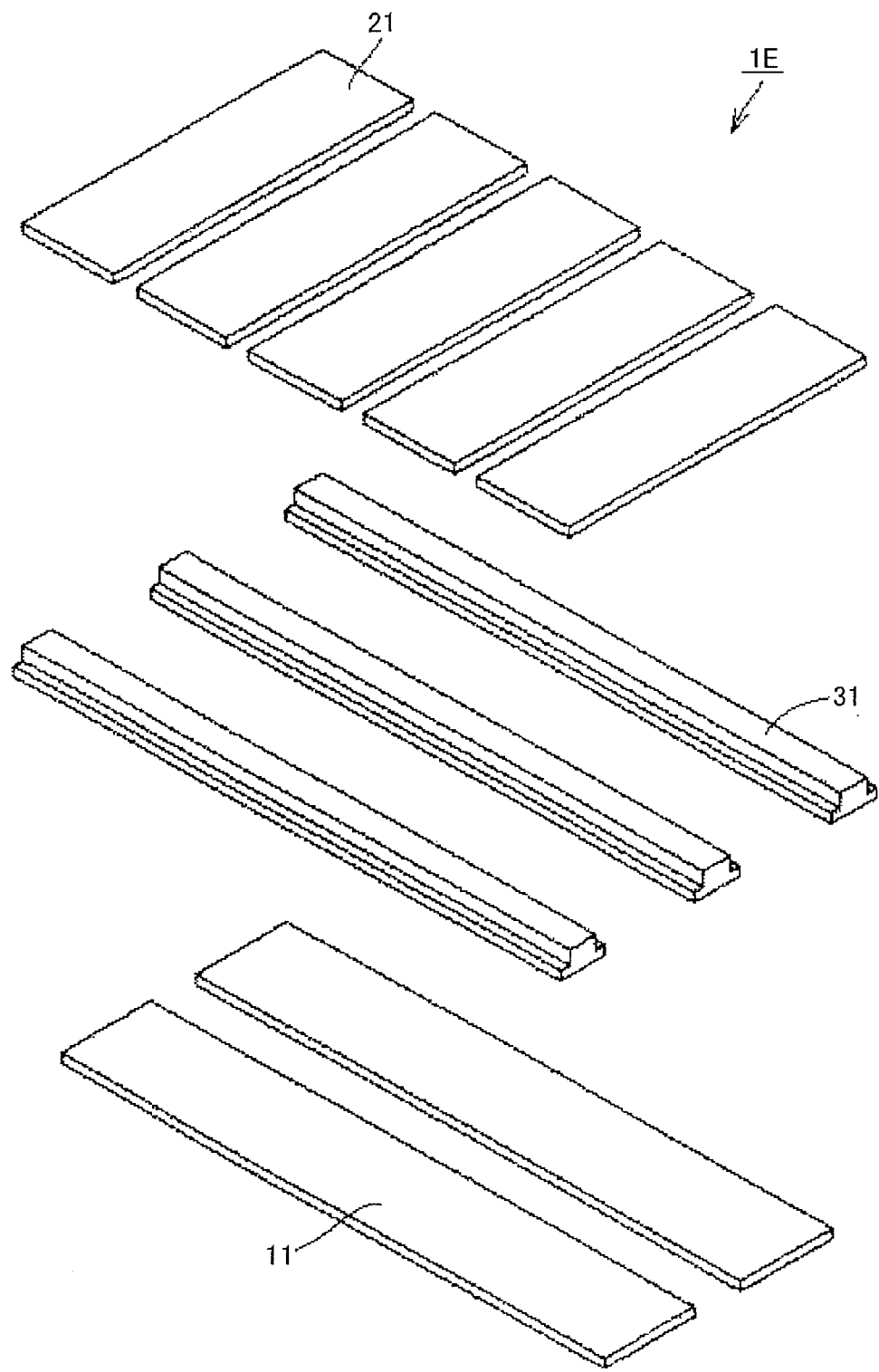
FIG. 27 is an exploded perspective view of the pressure detection section included in the capacitance pressure sensor illustrated in FIG. 26.
Figure 28:
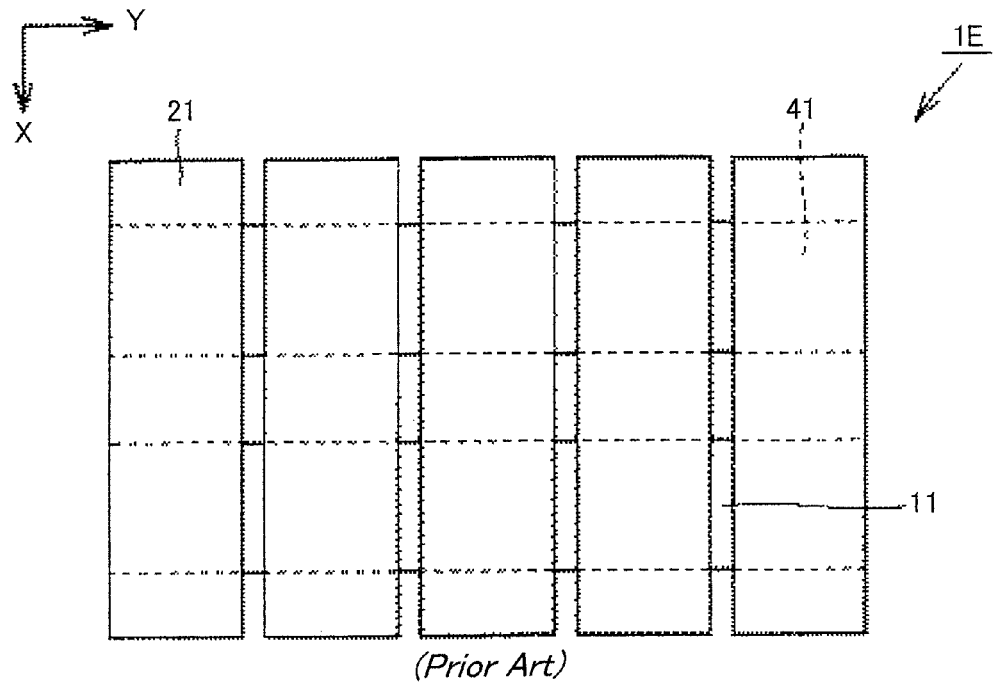
FIG. 28 (a) is a top plan view of the pressure detection section illustrated in FIG. 26.
Figure 28:
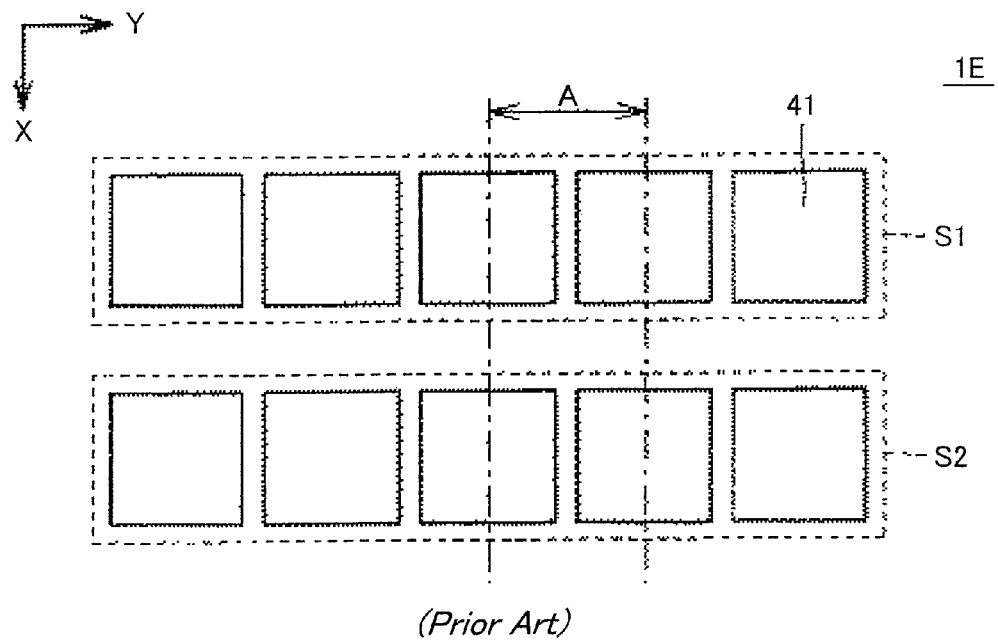
Figure 29:
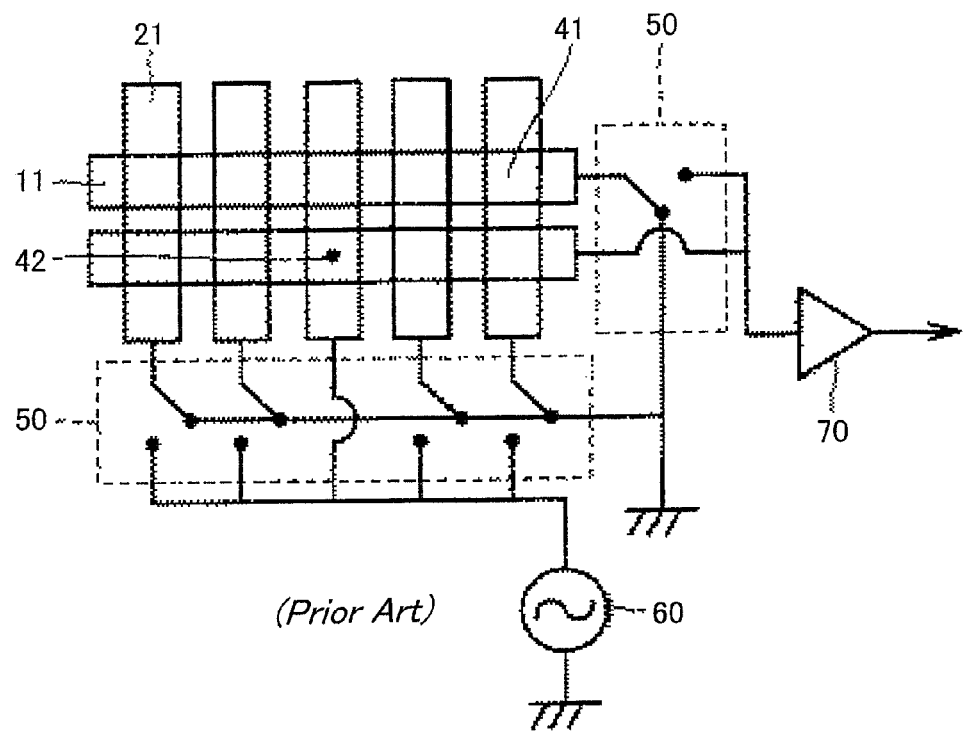
FIG. 29 is a circuit diagram of the capacitance pressure sensor including the pressure detection section illustrated in FIG. 26.
Figure 30:
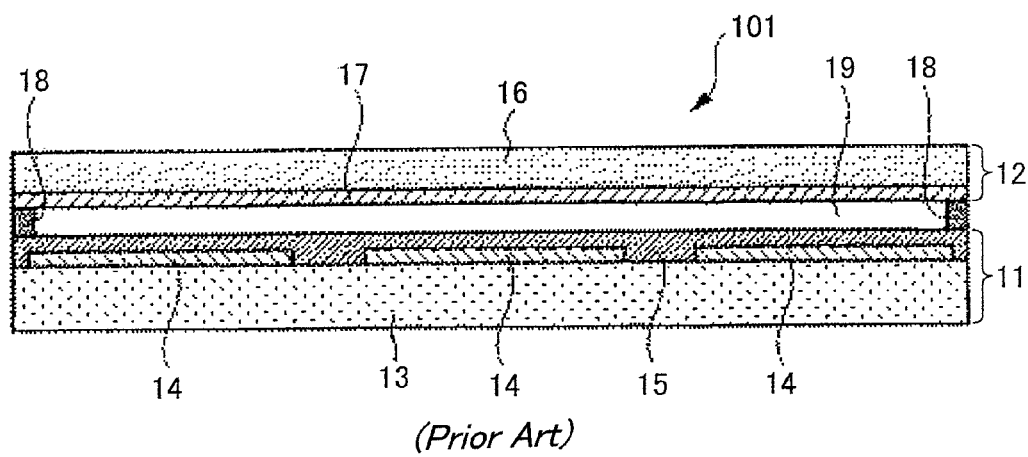
FIG. 30 is a view illustrating a schematic arrangement of a conventional surface pressure distribution sensor.
Figure 31:
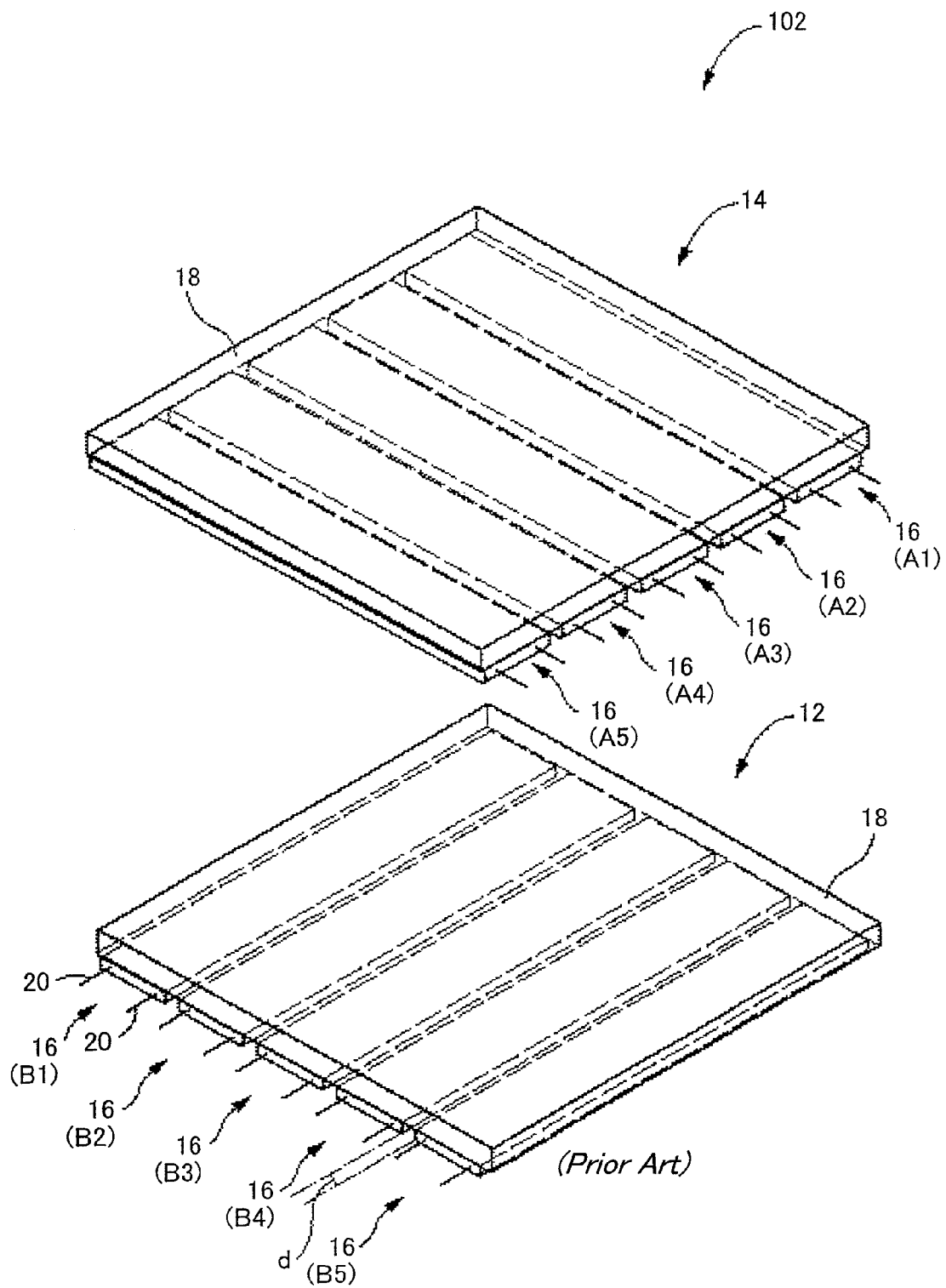
FIG. 31 is a view illustrating a schematic arrangement of a conventional pressure pulse wave sensor.
Figure 32:
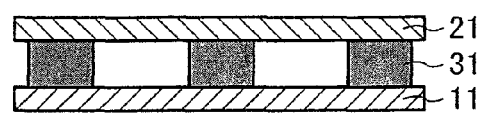
FIG. 32 is a side view of the capacitance pressure sensor illustrated in FIG. 26, (a) illustrates a side surface of the pressure sensor in a normal state (flat state), and (b) illustrates a side surface of the pressure sensor in a curved state.
Figure 32:
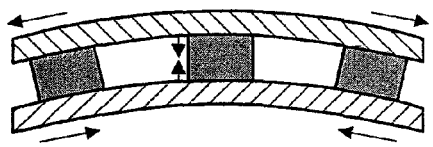

With reference to FIG. 25, another method for assembling the spacer 3 will now be described. FIG. 25 is a view illustrating steps for assembling the spacer 3. First, the gap stabilizing member 9 is brought into close contact with a release sheet including a PET film 9*a* and a release member 9*b* ((*a*) of FIG. 25). Next, only the gap stabilizing member 9 is cut by press working (half cut) so as to be formed in an arrayed manner ((b) of FIG. 25). The stabilizing member 9 is then placed on the movable-electrode-side substrate 2, and the release member is thermally cured so that the adhesiveness of the release member is reduced ((c) of FIG. 25). After that, the release sheet is removed ((d) of FIG. 25), whereby the making of the spacer 3 is complete. The array type capacitance sensor 40 can be produced by, after the completion, processing the spacer 3 so that the slits 3b are formed, placing the fixed-electrode-side substrate 5 on the spacer 3, and thermally curing the spacer 3.

The array type capacitance sensor 40 including the above spacer 3 is capable of having an effect similar to the array type capacitance sensor 30 of Embodiment 3. This is because the gap stabilizing member 9 has a similar function to the stabilizing member 8 described in Embodiment 3. Specifically, in a case where the array type capacitance sensor 40 is attached to a concavoconvex member, the movable electrodes 6 are deformed (bent) from the slits 3b and the gap stabilizing member 9, respectively. As such, it is possible to maintain the flexibility of the array type capacitance sensor 40, and to ensure the planarity of the movable electrodes 6 and the fixed electrodes 7, both of which constitute the capacitance elements. As a result, the array type capacitance sensor 40 of the present embodiment is capable of measuring a change in pressure with higher precision and reducing more cross talk.

As in Embodiment 2, the slits 2b in the movable-electrode-side substrate 2 may be extended to separate the individual strip-shaped movable electrodes 6 from one another so that the movable electrodes 6 are completely separated from one another.

The present invention is not limited to the description of the embodiments above, but may be altered by a skilled person within the scope of the claims. An embodiment based on a proper combination of technical means disclosed in different embodiments is encompassed in the technical scope of the present invention.

As described above, the array type capacitance sensor of the present invention is arranged such that the first substrate or the second substrate includes a substrate slit section provided between adjacent ones of the first electrodes or of the second electrodes, respectively, and that the substrate slit section has a slit shape, and extends in parallel with the first electrodes or in parallel with the second electrodes, respectively.

This prevents a specific one of the capacitance elements which one lies at a deformed portion of the array type capacitance sensor from being influenced by a portion of the first or second substrate and the first or second electrodes which portion is adjacent to the specific one of the capacitance elements. This allows providing an array type capacitance sensor capable of being produced inexpensively and measuring pressure precisely and stably even on a curved surface.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

Since the array type capacitance sensor of the present invention is capable of measuring a change in pressure precisely and stably, the array type capacitance sensor is applicable to a measurement of a minute change in pressure such as a measurement of pressure pulse wave of a living body.

The invention claimed is:

1. An array type capacitance sensor comprising:
   a first substrate including at least two rows of first electrodes provided so as to extend in parallel with one another;
   a second substrate, provided so as to face and be at a predetermined distance from the first substrate, including at least two columns of second electrodes which extend in parallel with one another in a direction crossing a direction in which the first electrodes extend; and
   a stabilizing member,
   the first substrate or the second substrate including a substrate slit section provided between adjacent ones of the first electrodes or of the second electrodes, respectively,
   the substrate slit section having a slit shape, and extending in parallel with the first electrodes or in parallel with the second electrodes, respectively,
   a spacer provided between the first substrate and the second substrate, except in spaces between respective opposite first and second electrodes, so as to maintain the predetermined distance,
   the spacer including spacer opening sections provided so as to extend, in a direction to intersect a longitudinal direction of the substrate slit section, in projection areas of the first or second electrodes onto the spacer, respectively,
   the first electrodes and the second electrodes being deformable in such a way that in an event that the first substrate or the second substrate is deformed, (i) the predetermined distance is maintained and (ii) adjacent ones of the first electrodes or of the second electrodes are deformable independently of one another.

2. The array type capacitance sensor according to claim 1, wherein the substrate slit section is provided in a direction at right angles to a direction in which the first substrate or the second substrate is bent during measurement.

3. The array type capacitance sensor according to claim 1, wherein the spacer includes a plurality of spacer slit sections, each having a slit shape, which are provided so as to extend, in parallel with the substrate slit section, in projection areas of the substrate slit section onto the spacer.

4. The array type capacitance sensor according to claim 1, further comprising a stabilizing member,
   the stabilizing member including grooves whose projection areas coincide with projection areas onto the substrate slit section, respectively, and the stabilizing member being provided, on a surface of the first substrate which surface is opposite to a surface facing the second substrate, or, on a surface of the second substrate which surface is opposite to a surface facing the first substrate.

5. The array type capacitance sensor according to claim 1, wherein the first or second substrate, which includes the substrate slit section, has flexibility.

6. The array type capacitance sensor according to claim 1, wherein the spacer has flexibility.

* * * * *